(12) United States Patent
Fan

(10) Patent No.: US 9,867,533 B2
(45) Date of Patent: Jan. 16, 2018

(54) SYSTEMS AND METHODS FOR DETERMINING AN ANGLE OF REPOSE OF AN ASYMMETRIC LENS

(71) Applicant: CooperVision International Holding Company, LP, St. Michael (BB)

(72) Inventor: Chi Shing Fan, Hong Kong (HK)

(73) Assignee: COOPERVISION INTERNATIONAL HOLDING COMPANY, LP, St. Michael (BB)

(*) Notice: Subject to any disclaimer, the term of this patent is extended or adjusted under 35 U.S.C. 154(b) by 70 days.

(21) Appl. No.: 15/070,254

(22) Filed: Mar. 15, 2016

(65) Prior Publication Data

US 2016/0287067 A1   Oct. 6, 2016

Related U.S. Application Data

(60) Provisional application No. 62/142,006, filed on Apr. 2, 2015.

(51) Int. Cl.
*A61B 3/14*    (2006.01)
*A61B 3/00*    (2006.01)
(Continued)

(52) U.S. Cl.
CPC .......... *A61B 3/0033* (2013.01); *A61B 3/0025* (2013.01); *A61B 3/0058* (2013.01);
(Continued)

(58) Field of Classification Search
CPC .......... A61B 3/14; A61B 3/102; A61B 3/107; A61B 3/13; A61B 3/0091; A61B 3/18; A61B 3/0041
(Continued)

(56) References Cited

U.S. PATENT DOCUMENTS 5,686,981 A    11/1997   Anan et al.
5,926,252 A *  7/1999    Reyburn ............... A61B 3/135
                                                351/159.21
(Continued)

FOREIGN PATENT DOCUMENTS

CA           2717328 A1       4/2012
TW        201241781 A        10/2012
(Continued)

OTHER PUBLICATIONS

Bethke (Ed), "Smartphones Take on Astigmatism", Review of Ophthalmology, Jun. 5, 2014, 4 pages.
(Continued)

*Primary Examiner* — Hung Dang
(74) *Attorney, Agent, or Firm* — Haynes Beffel & Wolfeld LLP

(57) ABSTRACT

Technology to determine the angle of repose of a lens, such as the angle of repose of a contact lens on an eye, includes storing an image including the lens captured using a camera and executing graphical user interface logic. The graphical user interface logic includes a frame or frames including the captured image, and graphical constructs prompting input identifying a set of locations on the captured image that are usable to define a location of the lens in the image, and a location usable to define an angle of repose of the lens in the image. The input data accepted via the graphical user interface is processed to determine angle of repose of the lens. The angle of repose of the lens is used to produce a specification for a lens.

24 Claims, 20 Drawing Sheets

(51) Int. Cl.
*G06T 11/60* (2006.01)
*H04N 5/232* (2006.01)
*G02C 7/02* (2006.01)
*G02C 7/04* (2006.01)
*G06T 7/73* (2017.01)

(52) U.S. Cl.
CPC .............. *A61B 3/14* (2013.01); *G02C 7/021* (2013.01); *G02C 7/04* (2013.01); *G02C 7/047* (2013.01); *G02C 7/048* (2013.01); *G06T 7/73* (2017.01); *G06T 11/60* (2013.01); *H04N 5/23216* (2013.01); *H04N 5/23293* (2013.01); *G06T 2207/10004* (2013.01); *G06T 2207/20101* (2013.01); *G06T 2207/20221* (2013.01); *G06T 2207/30041* (2013.01)

(58) Field of Classification Search
USPC .............. 351/211, 246, 247, 205, 200, 206
See application file for complete search history.

(56) References Cited

U.S. PATENT DOCUMENTS 5,963,299 A    10/1999  Reyburn
8,967,488 B2   3/2015   Pugh
2015/0061990 A1  3/2015  Toner et al.

FOREIGN PATENT DOCUMENTS

TW    201433998 A    9/2014
WO    2013104353 A1  7/2013
WO    2014193798 A1  12/2014

OTHER PUBLICATIONS

PCT Written Opinion Report in related Application No. PCT/GB2016/050824 dated Mar. 9, 2017, 11 pages.
TW 105110659—First Office Action dated Jan. 10, 2017, 26 pages.
PCT Search Report in related Application No. PCT/GB2016/050824 dated Jun. 24, 2016, 14 pages.
Office Action from family member application TW105110659, dated Jan. 10, 2017, with English translation, 26 pages.
PCT Int'l Preliminary Report on Patentability IPRP in related Application No. PCT/GB2016/050824 dated Jun. 26, 2017, 10 pages.
PCT Response to Written Opinon in related Application No. PCT/GB2016/050824 dated May 8, 2017, 13 pages.
TW 105110659—Office Action dated Aug. 9, 2017, 5 pages.

\* cited by examiner

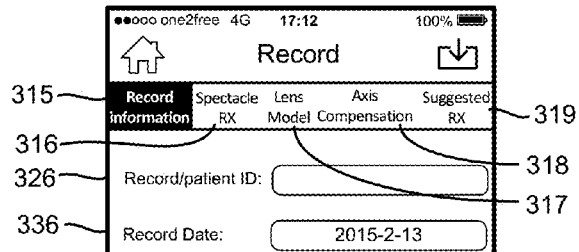
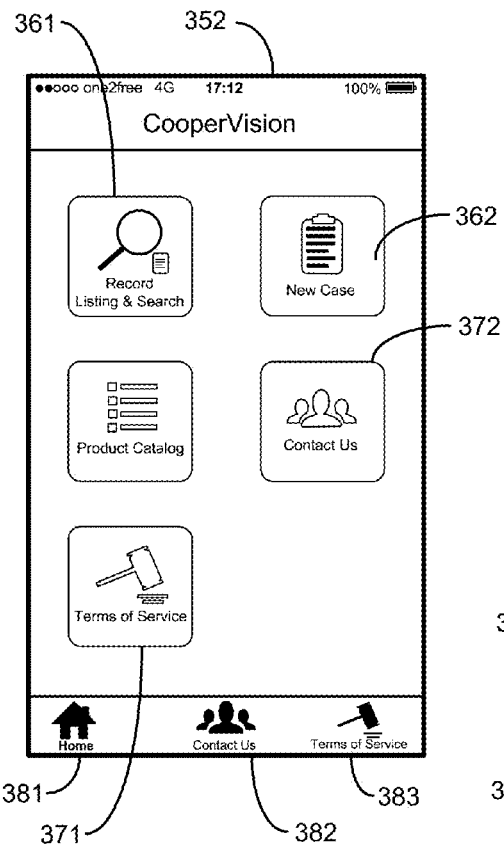
FIG. 3B
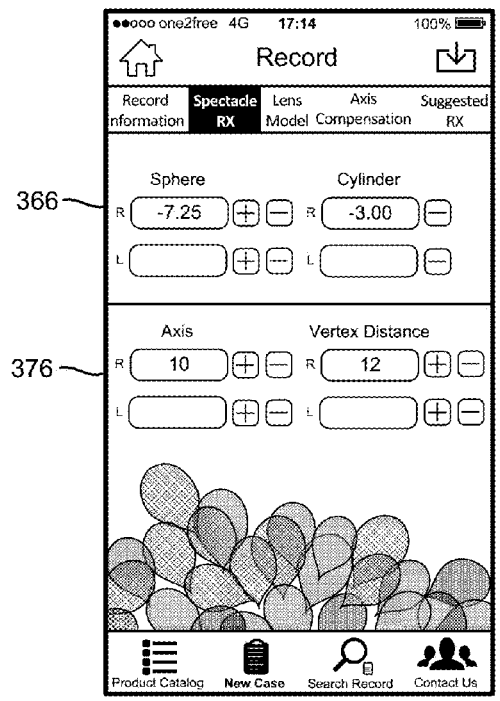
FIG. 3C
FIG. 3D

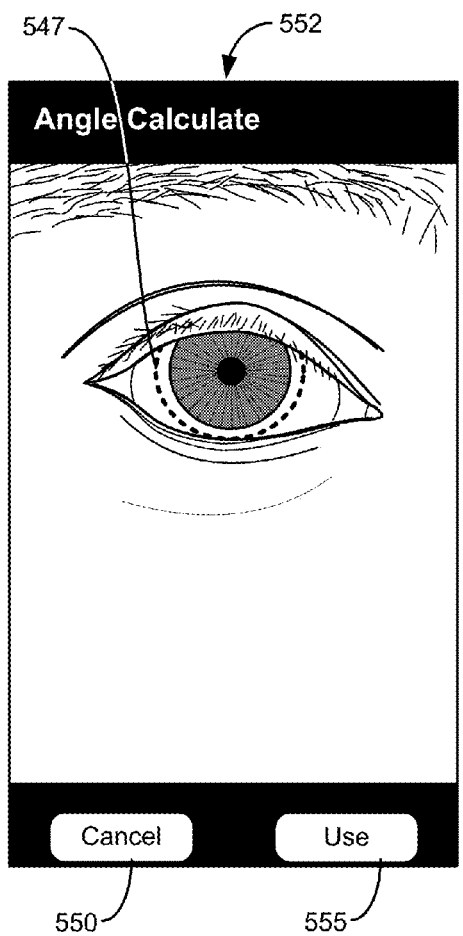
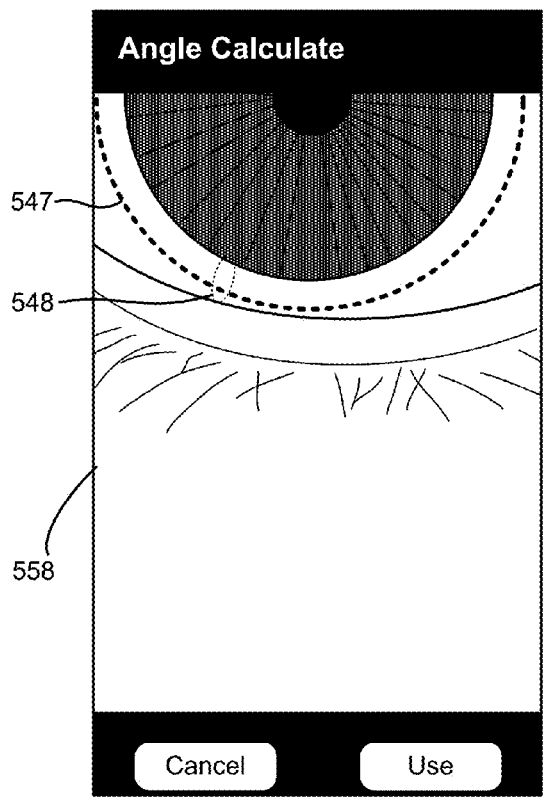
FIG. 5A
FIG. 5B

1100

| Minus Sphere | -0.75 | | -1.00 | | -1.25 | | -1.50 | | -1.75 | |
|---|---|---|---|---|---|---|---|---|---|---|
| | Sph | Cyl | Sph | Cyl | Sph | Cyl | Sph | Cyl | Sph | Cyl |
| 0.00 | 0.00 | -0.75 | 0.00 | -0.75 | 0.00 | -1.25 | 0.00 | -1.25 | 0.00 | -1.75 |
| -0.25 | -0.25 | -0.75 | -0.25 | -0.75 | -0.25 | -1.25 | -0.25 | -1.25 | -0.25 | -1.75 |
| -0.50 | -0.50 | -0.75 | -0.50 | -0.75 | -0.50 | -1.25 | -0.50 | -1.25 | -0.50 | -1.75 |
| -0.75 | -0.75 | -0.75 | -0.75 | -0.75 | -0.75 | -1.25 | -0.75 | -1.25 | -0.75 | -1.75 |
| -1.00 | -1.00 | -0.75 | -1.00 | -0.75 | -1.00 | -1.25 | -1.00 | -1.25 | -1.00 | -1.75 |
| -1.25 | -1.25 | -0.75 | -1.25 | -0.75 | -1.25 | -1.25 | -1.25 | -1.25 | -1.25 | -1.75 |
| -1.50 | -1.50 | -0.75 | -1.50 | -0.75 | -1.50 | -1.25 | -1.50 | -1.25 | -1.50 | -1.75 |
| -1.75 | -1.75 | -0.75 | -1.75 | -0.75 | -1.75 | -1.25 | -1.75 | -1.25 | -1.75 | -1.75 |
| -2.00 | -2.00 | -0.75 | -2.00 | -0.75 | -2.00 | -1.25 | -2.00 | -1.25 | -2.00 | -1.75 |
| -2.25 | -2.25 | -0.75 | -2.25 | -0.75 | -2.25 | -1.25 | -2.25 | -1.25 | -2.25 | -1.75 |
| -2.50 | -2.50 | -0.75 | -2.50 | -0.75 | -2.50 | -1.25 | -2.50 | -1.25 | -2.50 | -1.75 |
| -2.75 | -2.75 | -0.75 | -2.75 | -0.75 | -2.75 | -1.25 | -2.75 | -1.25 | -2.75 | -1.75 |
| -3.00 | -3.00 | -0.75 | -3.00 | -0.75 | -3.00 | -1.25 | -3.00 | -1.25 | -3.00 | -1.75 |
| -3.25 | -3.25 | -0.75 | -3.25 | -0.75 | -3.25 | -1.25 | -3.25 | -1.25 | -3.25 | -1.75 |
| -3.50 | -3.50 | -0.75 | -3.50 | -0.75 | -3.50 | -1.25 | -3.50 | -1.25 | -3.50 | -1.75 |
| -3.75 | -3.75 | -0.75 | -3.75 | -0.75 | -3.75 | -1.25 | -3.75 | -1.25 | -3.75 | -1.75 |
| -4.00 | -3.75 | -0.75 | -3.75 | -0.75 | -3.75 | -1.25 | -3.75 | -1.25 | -3.75 | -1.75 |
| -4.25 | -4.00 | -0.75 | -4.00 | -0.75 | -4.00 | -1.25 | -4.00 | -1.25 | -4.00 | -1.25 |
| -4.50 | -4.25 | -0.75 | -4.25 | -0.75 | -4.25 | -0.75 | -4.25 | -1.25 | -4.25 | -1.25 |
| -4.75 | -4.50 | -0.75 | -4.50 | -0.75 | -4.50 | -0.75 | -4.50 | -1.25 | -4.50 | -1.25 |
| -5.00 | -4.75 | -0.75 | -4.75 | -0.75 | -4.75 | -0.75 | -4.75 | -1.25 | -4.75 | -1.25 |
| -5.25 | -5.00 | -0.75 | -5.00 | -0.75 | -5.00 | -0.75 | -5.00 | -1.25 | -5.00 | -1.25 |

1155

Astigmatism Measurement from Spectacle Rx

*FIG. 11*

SYSTEMS AND METHODS FOR DETERMINING AN ANGLE OF REPOSE OF AN ASYMMETRIC LENS

RELATED APPLICATIONS

This application claims benefit of U.S. Provisional Patent Application No. 62/142,006 filed on 2 Apr. 2015.

BACKGROUND

The present technology relates to tools for measuring and analyzing the orientation of a toric lens, or other lens not radially symmetric, disposed on a patient's eye or other element on which the lens is disposed, and for modifying specifications for the lens based on the measurement.

A problem arises when fitting a contact lens for a patient when the lens is not radially symmetric. In particular, a lens that is not radially symmetric, such as a toric lens, is designed to be oriented at a specific angle relative to the eye. However, when placed on the eye, the lens may rotate to an angle of repose on the eye that varies from eye to eye. If the angle of repose is sufficiently different than the specified angle for the lens, then the lens will be ineffective or uncomfortable for the wearer.

One of the steps in fitting asymmetric lenses is to determine whether the lens rotates on the eye and the amount of rotation. Eye care professionals (ECP) have used an expensive special instrument known as a slit lamp to determine the angle of repose of the lens on a patient's eye. Toric lenses, for example, typically have an index mark on the lens outside the optic region that can be viewed using the slit lamp, as an indication of the angle of repose. The ECP can estimate the angle of repose based on the location of the index mark, and make adjustments to the specification for the lens. A slit lamp, however, is expensive and requires specialized training. It is desirable, therefore, to provide an easy to use technology to measure and analyze the orientation of lenses on eyes.

SUMMARY

Technology described herein includes systems and methods for computing the angle of repose for a lens, and for modifying a specification of a lens, such as an asymmetric lens, using the angle.

A method for operating a device or devices is described to determine the angle of repose of a lens, such as the angle of repose of a contact lens on an eye. The device or devices include a display, a data processor and a user input device such as a touchscreen overlying the display, such as commonly found on so-called "smart" phones. The method of operating includes storing an image including the lens captured using a camera and executing graphical user interface logic using the display. Graphical user interface logic includes a frame or frames including the captured image, and graphical constructs prompting input identifying a set of locations on the captured image that are usable to define a location of the lens in the image, and a location usable to define an angle of repose of the lens in the image. The graphical user interface logic accepts input data responsive to the graphical constructs that is interpreted as identifying locations on the captured image.

The device or devices can include a camera with an orientation sensor. The method can include displaying an orientation graphic on the display using the orientation sensor. The orientation graphic can include indicators of an orientation of a camera lens, or other indicators usable in composition of an image to be captured by the camera for use in the process. For example, the orientation graphic can include a graphical construct that indicates orientation of the camera lens around a line of site axis normal to the camera lens, around a horizontal axis and around a vertical axis.

The method can include processing the input data accepted via the graphical user interface to determine an angle of repose of the lens. Also, the method can include using the angle of repose of the lens to produce a specification for a lens, such as a contact lens prescription, based on the determined angle of repose.

Technology described herein also includes a device configured to execute processes as described above. Also, technology described herein includes a computer program product comprising a non-transitory computer readable medium storing instructions executable by a data processor that comprises logic to execute the processes described above.

Other aspects and advantages of the technology described herein can be seen on review of the drawings, the detailed description and the claims, which follow.

BRIEF DESCRIPTION OF THE DRAWINGS

The included drawings are for illustrative purposes and serve only to provide examples of possible structures and process operations for one or more implementations of this disclosure. These drawings in no way limit any changes in form and detail that may be made by one skilled in the art without departing from the spirit and scope of this disclosure. A more complete understanding of the subject matter may be derived by referring to the detailed description and claims when considered in conjunction with the following figures, wherein like reference numbers refer to similar elements throughout the figures.

FIG. 3B is an example frame of a of a graphical user interface for the top control level of a toric lens prescription device.

FIG. 3C is an example frame of a graphical user interface for the record information for a toric lens prescription device.

FIG. 3D is an example frame of a graphical user interface for the spectacle Rx input for a toric lens prescription device.

FIG. 5A shows an example portion of a frame of a graphical user interface including a view of a captured image.

FIG. 5B shows an example portion of a frame of a graphical user interface including a view of a captured image, including a zoom feature.

FIG. 11 shows a lookup table example for converting components of a spectacle prescription to a toric lens prescription.

DETAILED DESCRIPTION

The following detailed description is made with reference to the figures. Sample implementations are described to illustrate the technology disclosed, not to limit its scope, which is defined by the claims. Those of ordinary skill in the art will recognize a variety of equivalent variations on the description that follows.

The generation of the angle of repose for a lens on an eye, and methods for modifying a specification of a contact lens prescription using the angle will be discussed primarily with reference to FIGS. 1-16.

Figure 1:
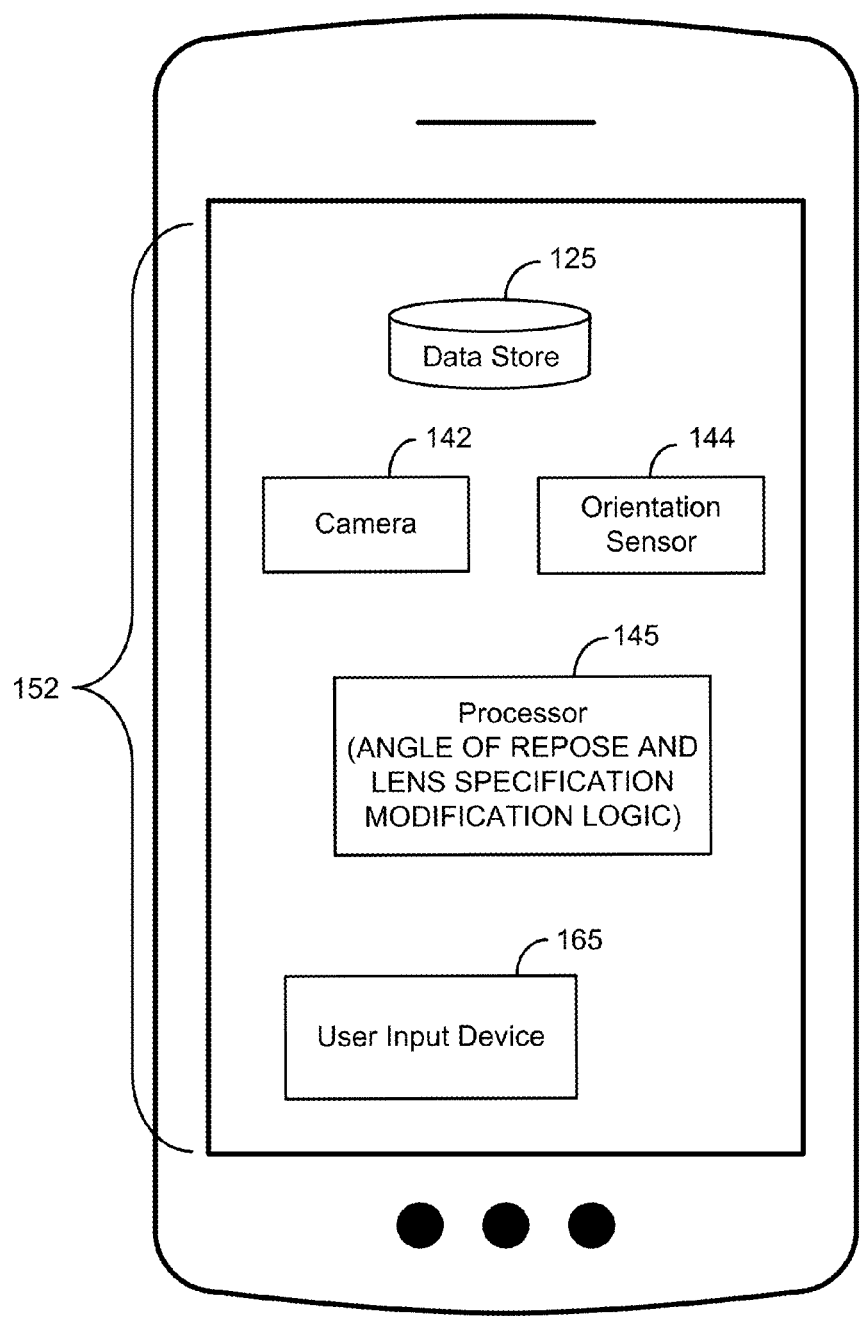
FIG. 1 illustrates one implementation of a device configured of determining an angle of repose of an asymmetric lens (such as a toric contact lens), and for modifying a specification for the lens.

FIG. 1 illustrates mobile phone 100 having a camera 142, a processor 145, a user input device 165 such as a touch screen, a display 152, an orientation sensor 144, and a data store 125. The mobile phone 100 is configured with instructions on a non-transistor computer readable medium executable by the processor 145 to provide a graphical user interface, and that include logic supporting the determination of the angle of repose of a lens which in some embodiments is combined with logic for modification of a specification of a lens using the determined angle. A mobile phone 100 is one example of a device that can be used with the present technology. Of course, one or more devices that include, or have access to, the basic components necessary can be utilized. For example, the camera, orientation sensor and the processor which executes portions of the graphical user interface can be implemented on more than one chassis, with data transfer capability by which for example the processor can execute logic to store an image captured by the camera.

Figure 2A:
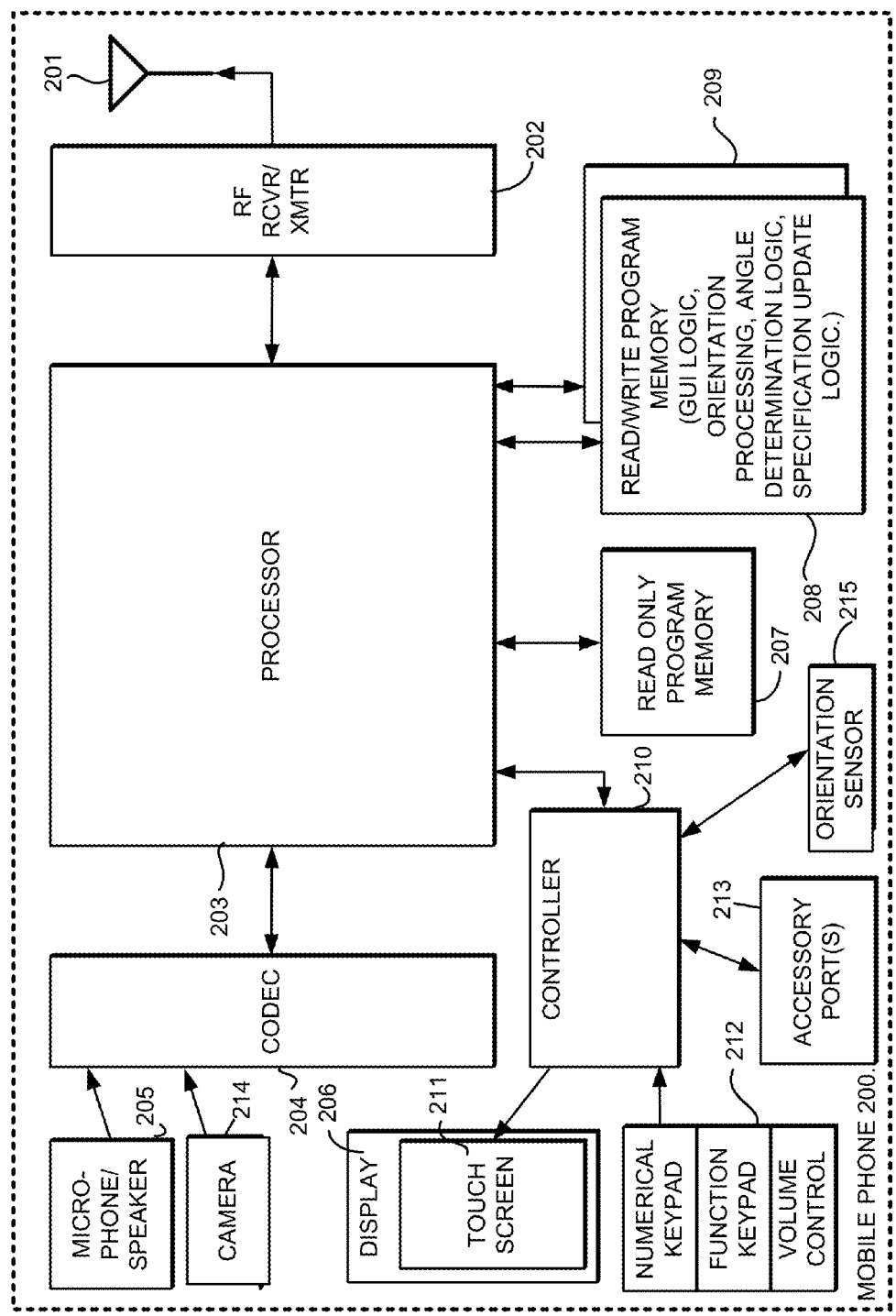
FIG. 2A is a block diagram for one implementation of a device like that of FIG. 1.

FIG. 2A is a simplified block diagram of a component of a mobile phone 200, representative of a device which can be implemented on a single chassis including tools described herein for measuring the angle of repose for a lens on an eye which in some embodiments is combined with logic for modification of a specification of a lens using the determined angle.

The mobile phone 200 in this example includes a camera 214, a display 206, with a touch screen 211 overlying the display, and a codec 204, including analog-to-digital and digital-to-analog converters coupled to the processor 203 which can execute instructions stored in memory on the device or accessible using the device. A view finder image is displayed on the display with the touch screen. Read-only memory 207 stores instructions, parameters and other data for execution by the processor 203. In addition, a read/write memory 208 in the mobile phone stores instructions, parameters, patient records, spectacle and contact lens prescriptions and other data for use by the processor 203. Also, the memory 208 in this example stores GUI logic, orientation processing logic, angle determination logic, specification update logic, and so on as described in more detail herein. There may be multiple types of read/write memory on the phone 200, such as nonvolatile read/write memory 208 (flash memory or EEPROM for example) and volatile read/write memory 209 (DRAM or SRAM for example). Other embodiments include removable memory modules in which instructions, parameters and other data for use by the processor 203 are stored. The mobile phone 200 includes a microphone/speaker 205, a radio including an RF receiver and transmitter 202 and an antenna 201, which supports audio and data communications.

An input/output controller 210 is coupled to user input devices including a touch screen 211 overlying the display 206, and to other user input devices 212, such as a numerical keypad, a volume control and a function keypad. The controller 210 in this example is also connected to and provides control functions for, an accessory port (or ports) 213, and an orientation sensor 215. In one embodiment, the orientation sensor is a three axis accelerometer such as commonly used on mobile phones.

The accessory port or ports 213 are used for other types of input/output devices, such as connections to processing devices such as PDAs, or personal computers, alternative communication channels such as an infrared port, a Bluetooth network interface, a Universal Serial Bus USB port, a portable storage device port, and other things. The controller 210 is coupled to the processor 203.

User input concerning patient records, including spectacle Rx and lens model information, is received via the input devices 212, the radio and/or other accessories. User interaction is enhanced, and the user is prompted to interact, using the touch screen 211 and display 206 and optionally other accessories.

In other implementations, mobile phone 200 may not have the same elements or components as those listed above and/or may have other/different elements or components instead of, or in addition to, those listed above, such as a web browser user interface, custom plugin engine, etc. The different elements or components can be combined into single software modules, and multiple software modules can run on the same hardware. Also, the present technology can be implemented on other types of devices.

Figure 2B:
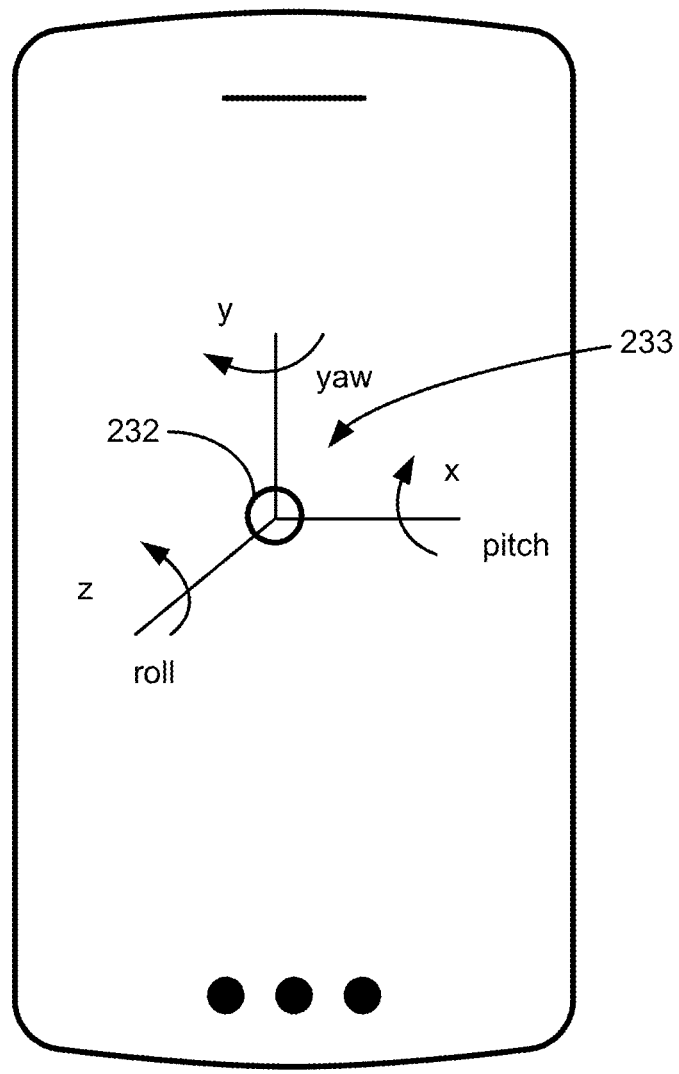
FIG. 2B displays alignment calculation example concepts for a device like that of FIG. 1.

The orientation sensor can include a three-axis accelerometer that can be used to indicate the orientation of the lens of the camera on the device. FIG. 2B illustrates one example of the location of a camera lens 232 on a side of a mobile phone 100 opposite the display. This location is more typically on the upper left corner of the mobile phone chassis, but is placed in the center in this drawing. The lens has a line of sight axis generally along the nominal surface normal of the lens into the field of view of the camera, which is labeled the "z" axis in this diagram. Also, the orientation of the lens can be specified by a horizontal axis, labeled the "x" axis in this diagram, and a vertical axis, labeled the "y" axis in this diagram. The three axes intersect at right angles as indicated by the graph 233 at the center of the lens, for example. The rotation of the camera about the line of sight axis is commonly referred to as roll. The rotation of the camera about the horizontal axis is commonly referred to as pitch, and the rotation of the camera around the vertical axis is commonly referred as yaw. For aligning the camera 214 of the disclosed device, the processor 203 utilizes inputs from the orientation sensor 215, generating an alignment graphic that includes indicators of orientation of the camera around the line of sight axis (roll), around the horizontal axis (pitch), and around the vertical axis (yaw). In one implementation, processor 203 implements a three-dimensional animation API, CATransformMake3DRotation, using function CATransform3DRotate to generate a graphical construct that reflects the orientation of the camera as it is positioned for taking an image of the lens to be analyzed. Alternative methods for orientation for a camera could be used.

Figure 3A:
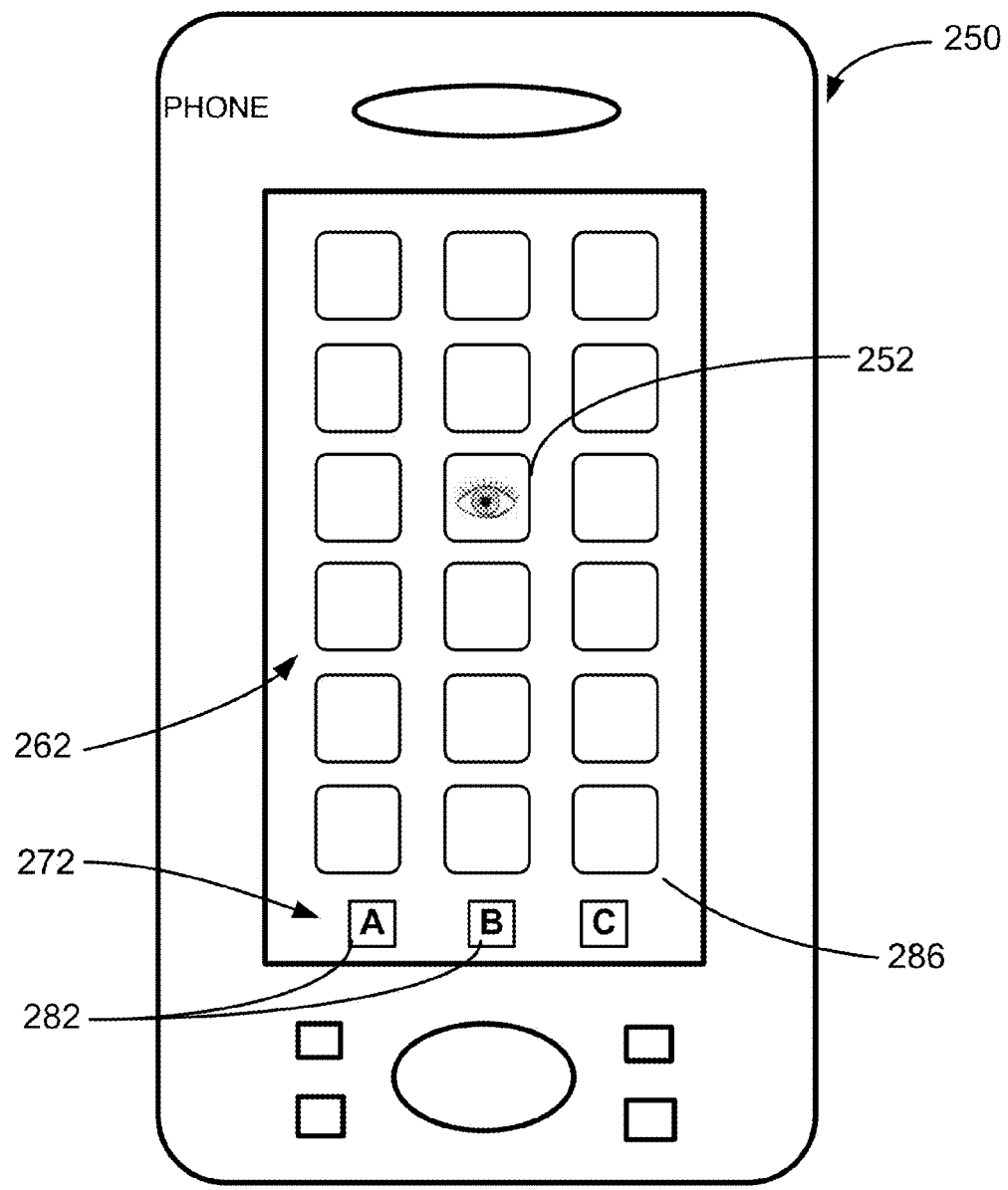
FIG. 3A is an example frame of a graphical user interface for a toric lens prescription device.

FIG. 3A illustrates a frame produced by a graphical user interface (GUI) logic displaying on the display 206. The frame includes a field 286 including a number of graphical constructs. The field 286 in this example includes a task bar 272 having system icons 282, used to select and invoke system operations. Also, the graphical constructs in field 286 can include a plurality of application icons 262 that, when selected by user input, can invoke corresponding applications in the device. In this example, the graphical constructs in field 286 include an eye icon 252 which, when selected, invokes logic to execute a graphical user interface as described herein.

Touching eye icon 252 can cause a program including graphical user interface logic stored in mobile phone 250 to be accessed; and to execute the graphical user interface logic. The graphical user interface logic can include interactive logic that includes displaying frames on the display, accepting input prompted by the graphical constructs on the frames, processing the input and then proceeding to a next frame or a next process.

In one example, the graphical user interface logic includes a frame having the screen image 352 shown in FIG. 3B. Screen image 352 includes application options such as record listing and search icon 361, new case icon 362, contact us icon 372, 382, terms of service 371, 383, and a construct 381 that includes a graphical home icon. An input generated by a touch on the touch screen over the new case icon 362 causes the graphical user interface logic to display a frame including the record information frame shown in FIG. 3C. The record information frame in this example includes a task bar including a construct 315 for "record information task," a construct 316 for a spectacle prescription task, a construct 317 for a lens model task, a construct 318 for an axis compensation task and a construct 319 for a suggested prescription task. As illustrated in FIG. 3C, selection of the Record Information task cause display of constructs that include text entry fields with labels that prompt entry of a patient ID in the record/patient ID field 326, and a date in the field 336. As shown in FIG. 3D, selection of the Spectacle RX task results in display of constructs that prompt user selection of various elements of a patient's spectacle prescription, including sphere and cylinder 366 and axis, and vertex distance 376.

Selection of the lens model construct 317 activates a list of lens brands and models, with a selector for choosing a model. Selection of the axis compensation construct 318 application icon activates the angle of repose calculation processes, and displays the angle rotation results. Selection of the suggested Rx construct 319 activates the prescription conversion process for converting the spectacle prescription plus angle of repose into contact lens prescription, described below.

The angle of rotation calculation processes in the graphical user interface logic include one or more frames to assist with centering and aligning the camera to compose an image of a lens disposed on the eye of the patient and capturing an image of the lens.

Figure 3E:
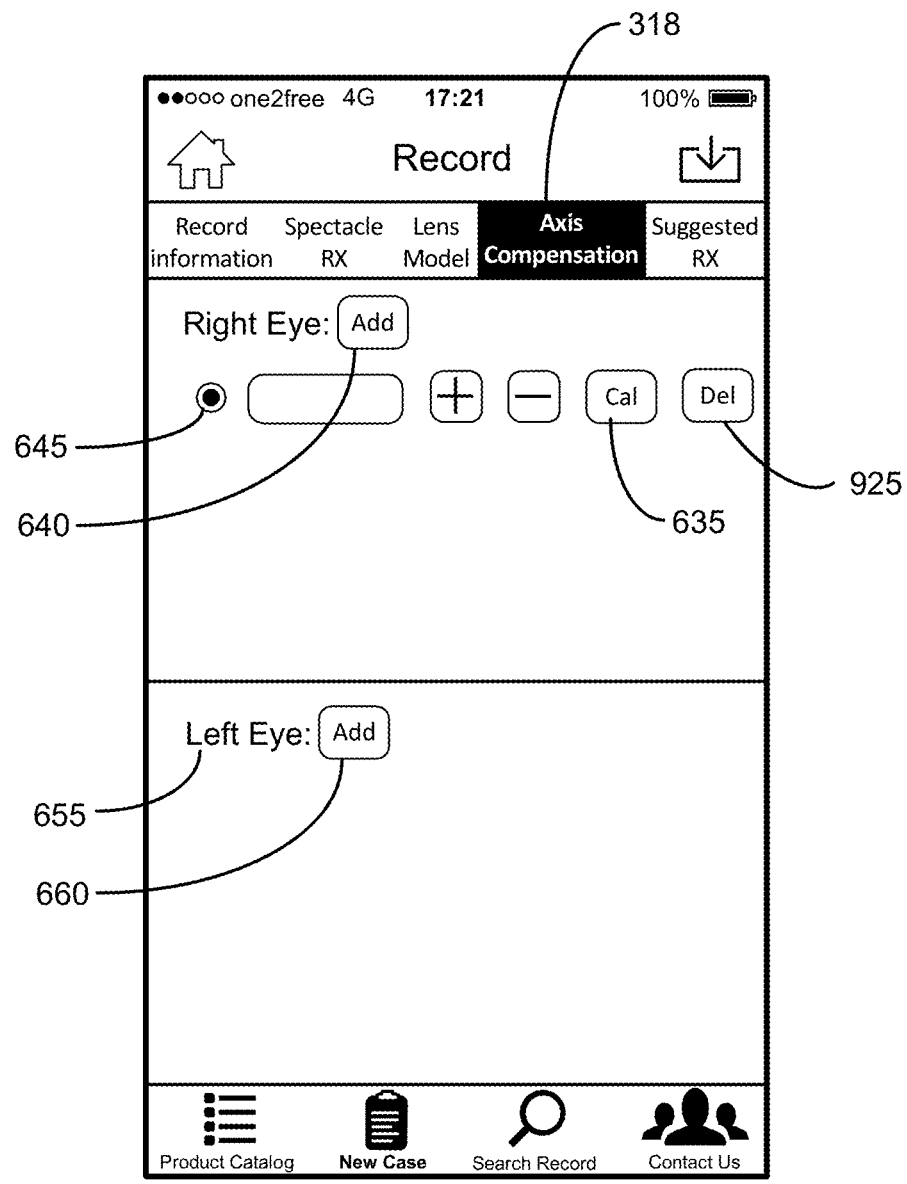
FIG. 3E shows an example frame showing an angle of repose display and GUI 'save' controls for a toric lens prescription device.

To capture an image, the user can hold the camera upright at the level of the eye of the patient, and utilize the graphical user interface to assist capturing an image of the eye. The graphical user interface logic can include a frame as shown in FIG. 3E, including graphical constructs for choosing right eye 645 or left eye 655. Other constructs on the frame shown in FIG. 3E can include buttons 640, 660 to activate an image capture mode for the left and right eyes, buttons (e.g. 635) used to activate an angle calculation mode (shown in FIG. 7), to add or subtract from a displayed value, and to cancel the procedure. Del icon 925 can be used to delete the angle measured. Input generated by selecting one of the eyes in the frame shown in FIG. 3E can then cause the graphical user interface to enter an image capture mode, in which a frame or sequence of frames like that shown in FIG. 4A is displayed.

Figure 4A:
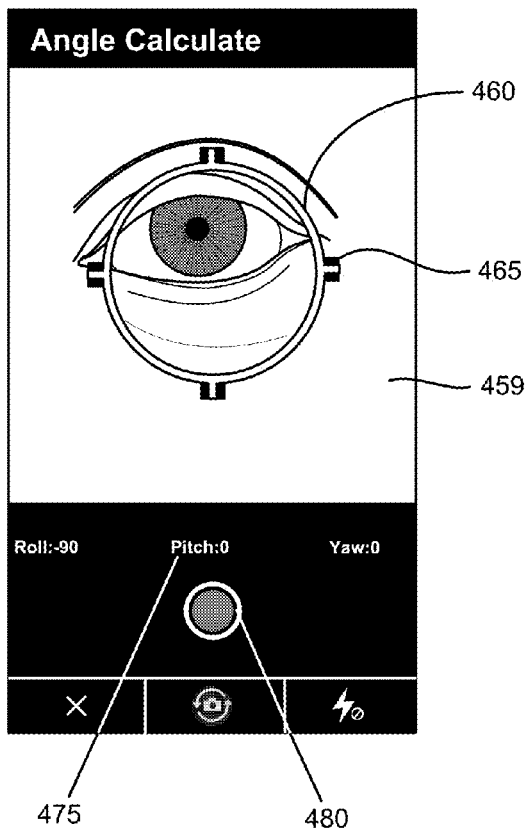
FIG. 4A shows an example frame of a graphical user interface including an orientation graphic.

The frame in FIG. 4A includes view finder field 459 in which an image from the camera view finder is displayed in real time on the touch screen 211. Also, it includes an image capture button (graphical construct 480) which, when selected, captures an image and stores the captured image for processing. In the example shown, the frame includes an orientation graphic comprising in this example a movable ellipsoid feature 460, which can be red for example, and a set 465 including one or more fixed marks which indicate a preferred orientation for the camera. Also, or in the alternative, the orientation graphic includes a feature useable as reference for sizing the lens subject of the measurements within the area of the captured image. For example, the orientation graphic can include a perceptible ellipsoid within which the user can position the lens and which can be used as a reference for magnification to adjust the size of the lens in the image to be captured.

The graphical user interface logic can generate the orientation graphic using the orientation sensor to indicate orientation of the camera around one or more of the line of sight axis, the horizontal axis and the vertical axis. In this example, the movable feature 460 has index marks located nominally at 12, 3, 6 and 9 o'clock. Also, in the example, the set 465 of one or more fixed marks includes alignment indexes which comprise pairs of lines positioned at 12, 3, 6 and 9 o'clock. When the camera is oriented as desired, the movable feature is positioned on the display so that the index marks align with the alignment indexes on the set 465 of one or more fixed marks. The frame illustrated in FIG. 4A can also include fields (e.g. 475) for displaying current angles of rotation for one or more of the roll, pitch and yaw.

Figure 4B:
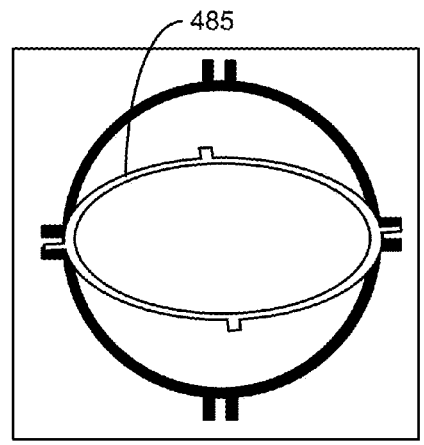
FIG. 4B shows an example frame of a graphical user interface including an orientation graphic when the camera is positioned at an oblique angle relative to the patient's eye.
Figure 4C:
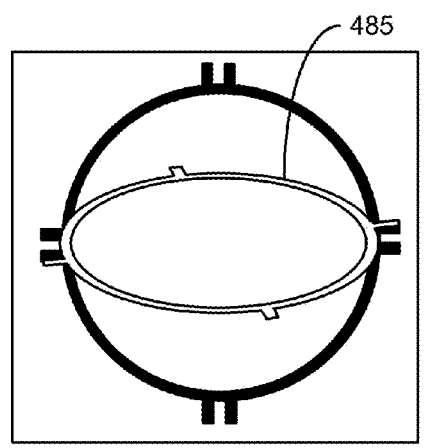
FIG. 4C shows an example portion of a frame of a graphical user interface including an orientation graphic as the camera is positioned at another oblique angle relative to the patient's eye.
Figure 4D:
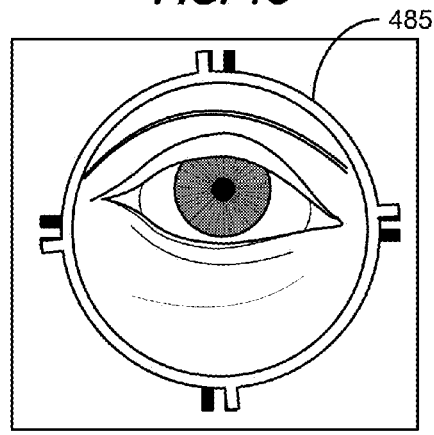
FIG. 4D shows an example portion of a frame of a graphical user interface including an orientation graphic when the camera is positioned slightly misaligned relative to the patient's eye.

In an example embodiment, the orientation graphic is generated in real time as the camera is moved. The shape of the movable feature 460 shifts as the position of the camera changes, as illustrated in FIGS. 4B, 4C and 4D. In FIG. 4B, the moveable feature 485 is presented as an ellipsoid having a long axis that is close to horizontal and reaches across the fixed circle, and a short axis that is offset from the vertical by a slight negative angle and substantially shorter than the diameter of the fixed circle. The length of the short axis indicates that the camera is rotated about the horizontal axis. The rotation of the long and short axes indicates a small offset around the line of sight axis. The length of the long axis indicates that the camera is close to preferred alignment on the vertical axis. In FIG. 4C, the moveable feature 485 is presented as an ellipsoid having a long axis that is slightly offset from the horizontal and reaches across the fixed circle, and a short axis that is offset from the vertical by an angle of close to 10 degrees and substantially shorter than the diameter of the fixed circle. The length of the short axis indicates that the camera is rotated about the horizontal axis. The rotation of the long and short axes indicates an offset around the line of sight axis. The length of the long axis indicates that the camera is close to preferred alignment on the vertical axis. In FIG. 4D, the moveable feature 485 is presented as an ellipsoid (now close to circular) having a long axis that is slightly offset from the horizontal, and reaches across the fixed circle, and a short axis that is slightly offset from the vertical and reaches across the fixed circle. As the length of the short axis and the long axis of the ellipsoid reach the diameter of the fixed circle, the orientation graphic indicates that the camera is aligned about the horizontal axis and vertical axis as desired. As the position of the indexes on the movable feature align with the alignment index marks on the fixed circle, orientation graphic indicates that the camera is aligned around the line of sight axis. In this manner, the graphical user interface logic can present feedback about the alignment of the camera to the user during the image capture mode.

The graphical user interface logic can continuously update and display these visual alignment indicators on display in overlying the view finder field 459 on the display 206. In some examples, the orientation graphics can be positioned differently on the frame or elsewhere viewable by the user, as suits a particular implementation. The processor 203 can calculate and display one or more of the pitch value (e.g. in field 475), roll value and yaw value, while the user adjusts the orientation by moving the camera until the one or more of the pitch, roll and yaw values display appropriate values.

Input generated by selection of the construct 480 on the frame shown in FIG. 4A causes capture and storing of the image. The captured image is stored in a manner that incorporates alignment information within the image, such as by having pixels with coordinates on the captured image. The alignment process supported by the graphical user interface logic can assist in producing an image that does not include keystone distortion that can interfere with the accuracy of the computations executed. Keystone distortion occurs for example when an image is projected on a surface that is not perfectly normal to the lens. This distortion can make accurate measurement of a rotation angle difficult or impossible. This keystone effect is seen in a projection of an image onto a surface at an angle, as with a projector whose line of projection of the image is not normal to the screen on which it projects. With the alignment tools presented herein, the processes can be based on an assumption that the captured image does not include significant keystone distortion, and that the coordinate axes used to identify locations in the image can be considered to correspond to a reference plane on the lens usable to determine its angle of repose.

In some implementations, the graphical user interface logic may only accept the graphical construct for capturing an image at times when the alignment meets some minimum criteria.

After storing a captured image, the graphical user interface logic can cause display of a frame like that shown in FIGS. 5A and 5B. The frame in FIG. 5A shows the captured image in field 552 and button constructs 550, 555 which, when selected, cause the view finder image to be used for angle computations, or to be discarded. The frame includes a zoom feature, which can be activated by a gesture using the touch screen, for example, so that a zoomed image 558 can be produced in the field 552. This feature permits the user to check quality (focus) of the captured view finder image to determine whether the lens edges (547) and the alignment index mark (548) on the lens can be seen. This feature can be used for sizing the lens within the area of the captured image. The alignment index mark 548 on a contact lens is typically a groove on the lens surface which can be seen by an ECP. A zoom feature on the device enables more accurate viewing of the feature.

Figure 7:
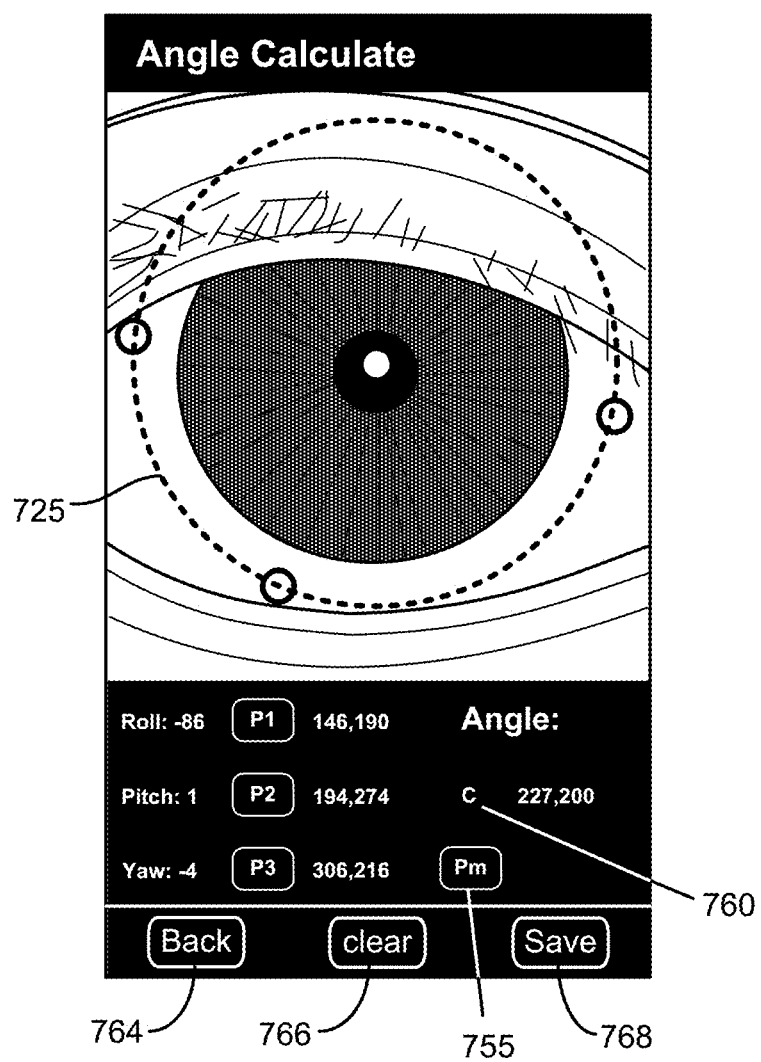
FIG. 7 shows an example frame of a graphical user interface including graphical constructs for prompting input of data and accepting input via a touch screen, with a zoom feature for the captured image.
Figure 8:
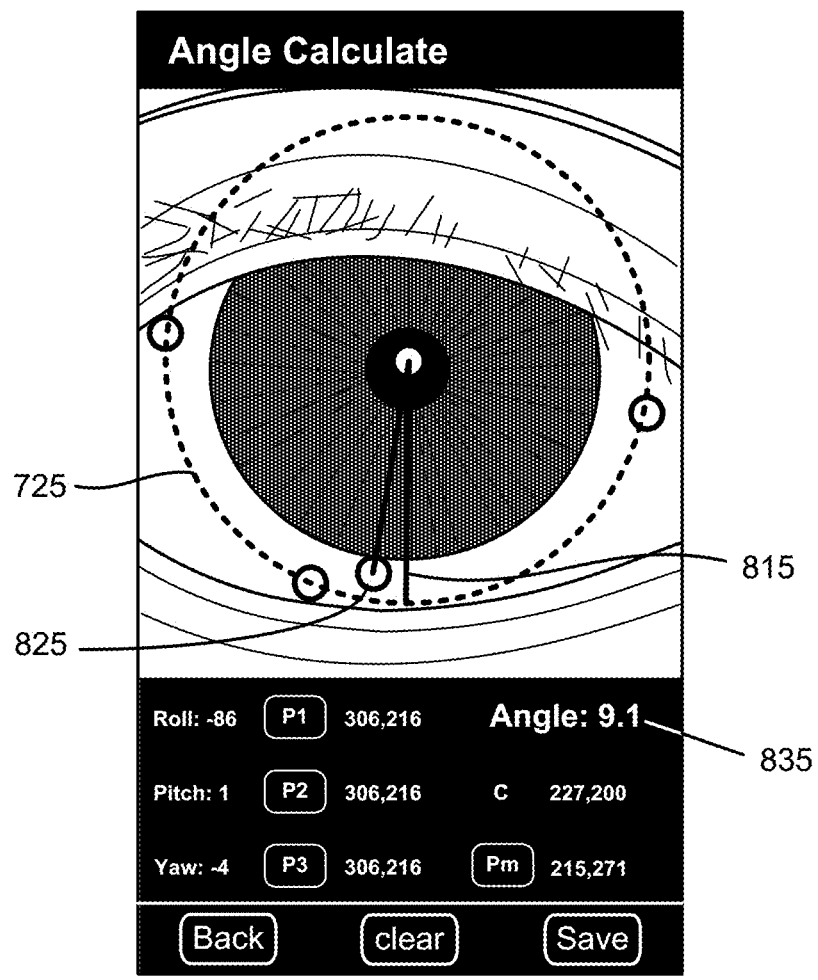
FIG. 8 shows an example frame of a graphical user interface including graphical constructs for prompting input of data and accepting input via a touch screen, including a construct for prompting input of a location on the captured image to indicate a location of an index mark on the lens.

After the graphical user interface logic stores an accepted eye image, the process continues to axis compensation, in which the graphical user interface uses the display, to present a frame or frames including the captured image, and graphical constructs prompting input identifying a set of locations on the captured image usable to define a location of a lens in the image, and a location usable to define an angle of repose of the lens in the image, and to accept input data responsive to the graphical constructs that identifies locations on the captured image. Also, the graphical user interface logic can process the input data to determine the angle of repose of the lens in the image. Example frames usable for this purpose are shown in FIGS. 6-8.

Figure 6:
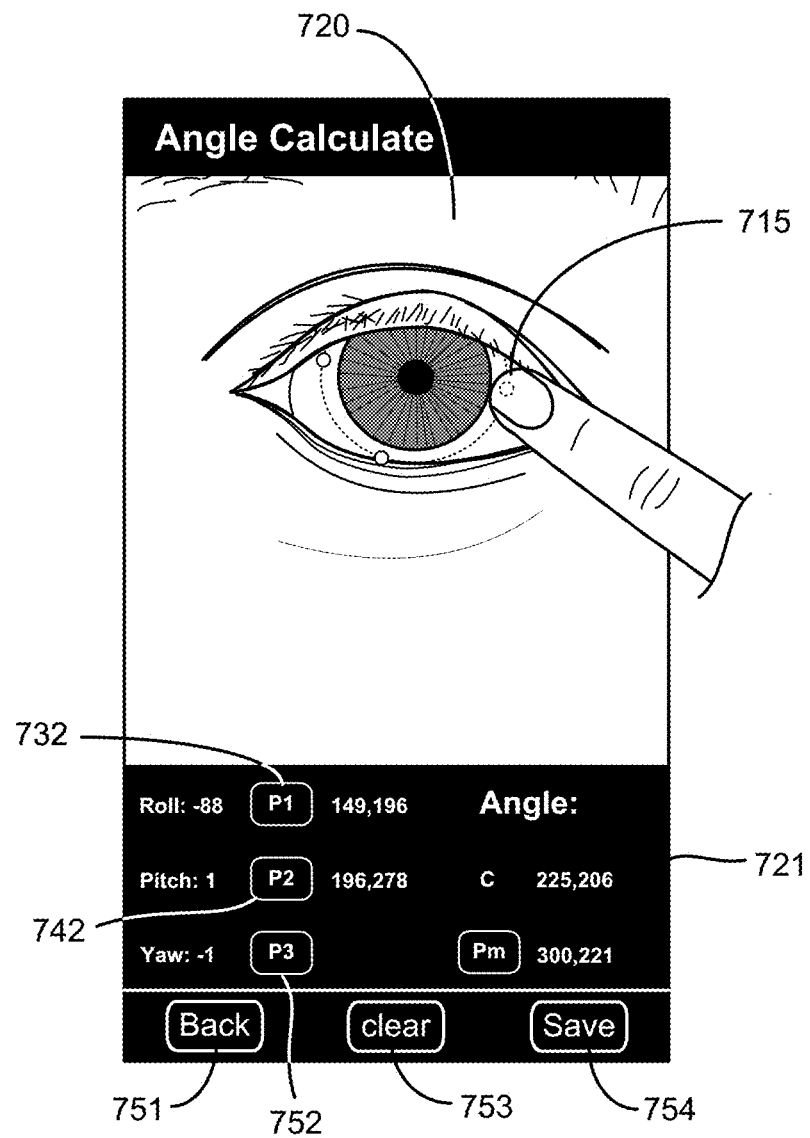
FIG. 6 shows an example frame of a graphical user interface including graphical constructs for prompting input of data and accepting input via a touch screen.

The frame shown in FIG. 6 includes a field 720 in which the captured image is displayed, and a field 721 including a set of graphical constructs. The graphical constructs in the field 721 prompt input identifying a set of locations, and include a construct (e.g. 732) which when selected identifies a particular member of the set of locations, and causes the graphical user interface to interpret coordinates of a selected point in the displayed image as the particular member of the set of locations. Other constructs 751, 753 and 754 are included, and used to invoke actions by the graphical user interface logic.

In this example, the constructs in field 721 include a set of constructs (e.g. 732, 742, 752) corresponding to locations usable to define a perimeter of the contact lens in the captured image, where the constructs in the set when selected identify respective members of the set of locations, and cause the graphical user interface to interpret coordinates of a selected point (e.g. point 715) selected by a user touch on the touch screen in the captured image as the respective member of the set of locations.

In this example, the constructs (e.g. 732, 742 and 752) are used to identify data that is interpreted as the locations of three points on the edge of a toric contact lens in the image, as selected by the user. The three selected points are interpreted by the graphical user interface logic as identifying the location of the circumference of the contact lens, usable in a process to define an angle of repose of the contact lens in the image. The graphical user interface logic can display values representing the coordinates of the locations of the three dots in fields P1 (construct 732), P2 (construct 742) and P3 (construct 742).

Also, the constructs in the field 721 include another construct 755 which corresponds to an index point location in the set of locations usable to define the location of an index point on the lens in the capture image. An index point can be the mark that is typically used on toric contact lenses, or any other feature of the lens that can indicate an angular position of the lens relative to a reference line, such as a vertical line. When selected, the construct 755 identifies the index point location, and causes the graphical user interface to interpret coordinates of a selected point in the captured image as the index point location in the set of locations.

The graphical user interface logic can produce a graphical element 725, as seen on FIG. 7, that overlays the circumference of the contact lens image, based on the 3 data points entered by the user. This location is usable to define an angle of repose of the contact lens in the image. The coordinates of the center of the circle can be displayed, if desired, as indicated by the field labeled with the construct "C" 760 in FIG. 7.

In one implementation, a widely understood method of defining a circle uses the perpendicular bisectors of two chords drawn between the 3 dots to calculate the center and radius of the circle. The circle represents the location of the lens in the image of the eye.

By processing the input interpreted as identifying the user-selected index mark, the graphical user interface logic calculates the angle from vertical axis (815) in the image from the center of the lens to the index mark (825), and interprets that angle as the angle of repose of the lens on the eye. The angle of repose of the lens on the eye can be displayed in the field 835 as illustrated in FIG. 8.

Figure 9:
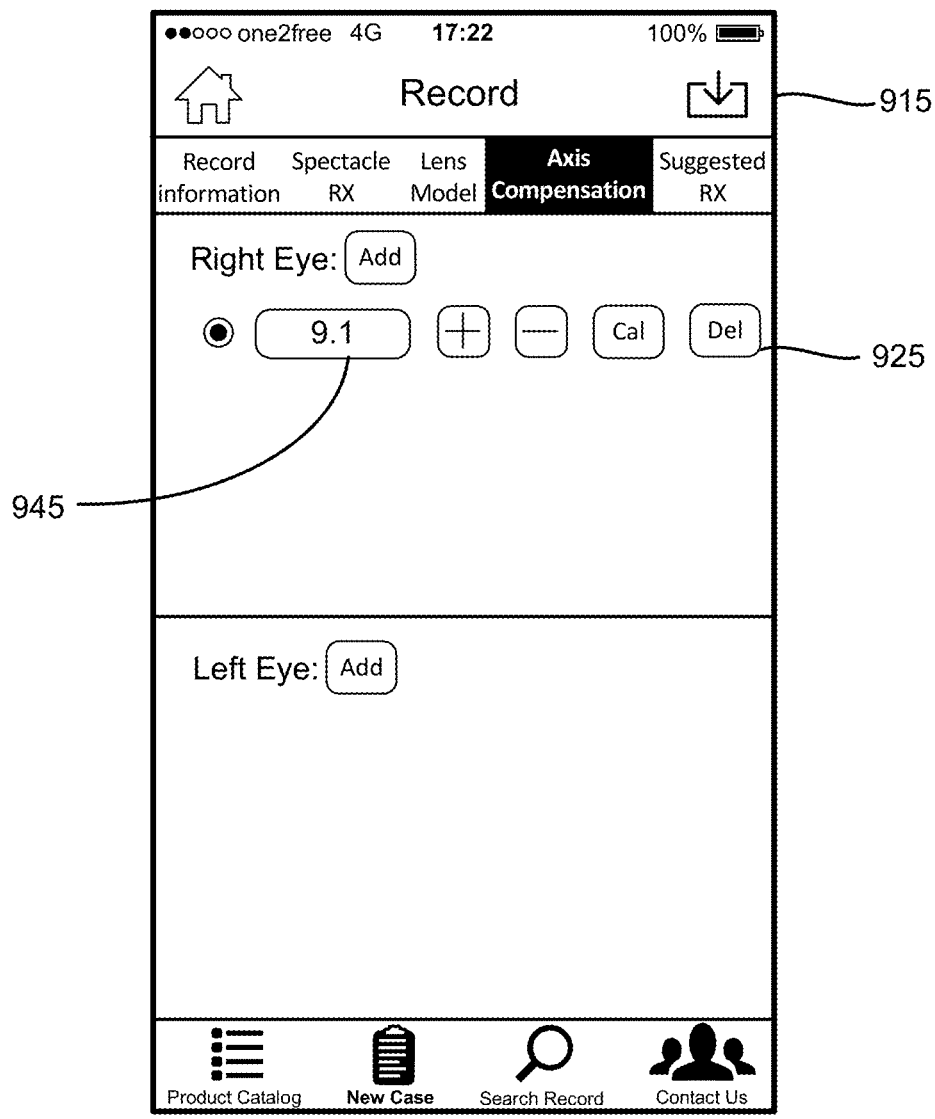
FIG. 9 shows an example frame of a graphical user interface including controls for left and right eyes, for axis compensation for a toric lens prescription device.

After computation of the angle of repose, the graphical user interface logic can display a frame like that of FIG. 3E, updated as shown in FIG. 9 to show the angle of lens repose in the user interface.

Figure 10A:
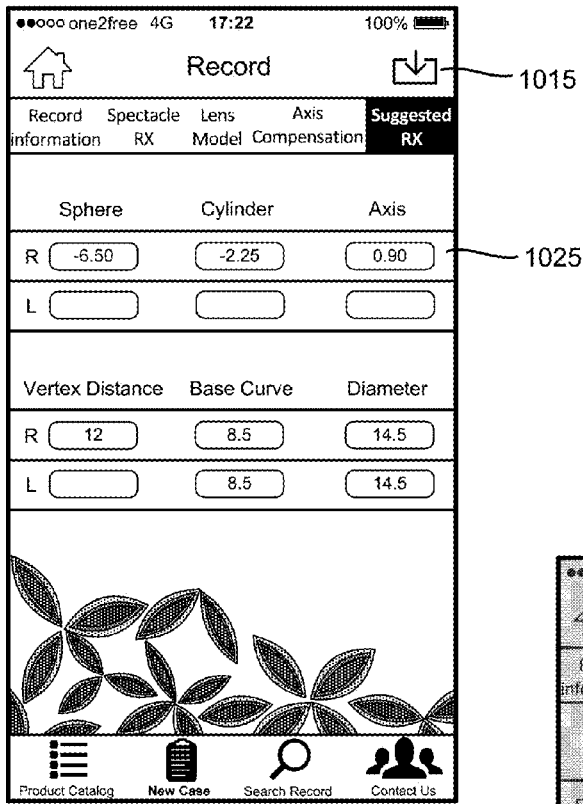
FIG. 10A shows an example frame of a graphical user interface including an example converted Rx for a toric lens prescription.
Figure 10B:
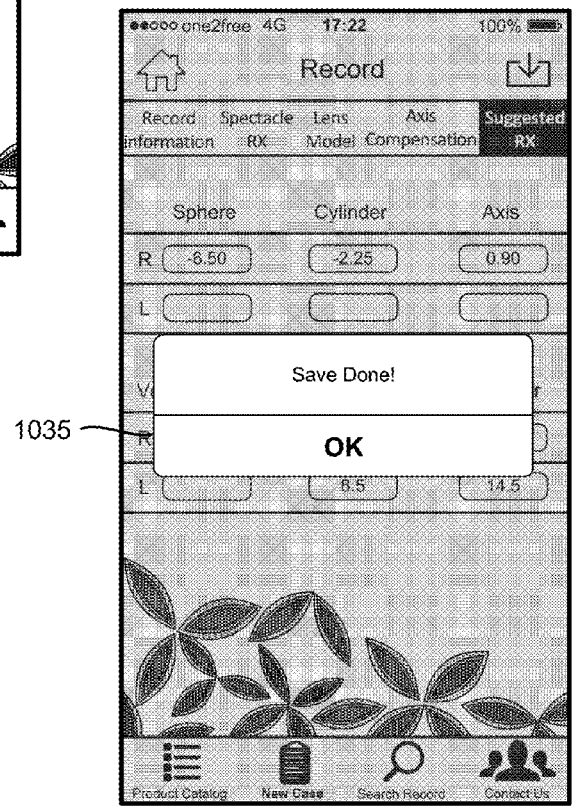
FIG. 10B shows an example frame of a graphical user interface including a graphical element for a completed 'save' function for a toric lens prescription.

From the screen shown in FIG. 9, the user can select a variety of processes as explained above. A suggested prescription process is invoked by selection of the construct 319. Upon selection of the construct 319, the graphical user interface logic can display a frame like that shown in FIG. 10A, which includes constructs 1025 for displaying updated specifications for a lens, including for example the sphere, cylinder and axis parameters of a toric contact lens prescription. Also, the frame shown in FIG. 10A includes construct 1015 which, when selected, invokes a process to save the lens specifications in the patient record. As shown in FIG. 10B, after a successful save operation, the graphical user interface logic can display a window 1035 indicating that the process is done.

In some implementations, the processor 203 can initiate transmission of the value of the angle of lens rotation for the patient to another processor, such as a smart phone, a tablet, a laptop computer or a desktop computer. Prescription entry and mapping can be completed by any of these devices.

In one example, the graphical user interface logic can include a lookup table and supporting logic to compute the updated specifications as follows. The logic receives user input concerning patient records, including spectacle Rx and lens model information, and an angle of lens rotation 945 for the patient. The angle of repose can be deleted using the Del icon 925, if the patient's measurements are to be updated. A contact lens prescription for a patient with astigmatism can include 3 components: degree of shortsighted or longsighted (i.e. −5.25), degree of astigmatism (i.e. −1.50) and location of the astigmatism (i.e. 10). Sphere measurements (y axis of table degree of shortsighted or longsightedness; i.e. −5.25) and degree of astigmatism (x axis of table; i.e. −1.50) can be used as indexes to entries in a lookup table 1100 stored in memory accessible by the processor, to determine two components of the suggested contact lens Rx (−5.00 −1.25) 1155. In an alternative example, the graphical user interface logic can include utilize formulae or combinations of formulae and tables to compute the updated specifications for the updated prescription.

Then the logic can calculate the axis of the suggested Rx using the convention that a positive value means the lens rotates to the left (rotates clockwise from user's viewpoint), and a negative value means that the lens rotates to the right in a counter-clockwise direction as specified by a rule called "Left Add, Right Subtract" (known as the LARS rule) or "Clockwise Add, Anticlockwise Subtract" (known as the CAAS rule). To calculate the axis of the suggested Rx:

Axis of suggested toric lens Rx=axis of the spectacle Rx+angle measured

For example, if the axis of the spectacle Rx=10°, and the angle of repose=−5°, then the axis of the suggested Rx=10°+ (−5°)=5°. The range of axis measurements is from 1 to 180 degrees, like a protractor; that is, 0=180; only 180° are in use for prescriptions. Any axis value greater than 180° is represented by the value on the "opposite" side. For example, an axis measurement of 181=1, 270=90, 320=140, etc. Therefore, if the axis of a spectacle Rx is 180 degrees, angle rotation measured is 20, the result of the suggested Rx is 20 because {180=0 (spectacle Rx)}+{20 (angle measured) }=20.

Figure 12:
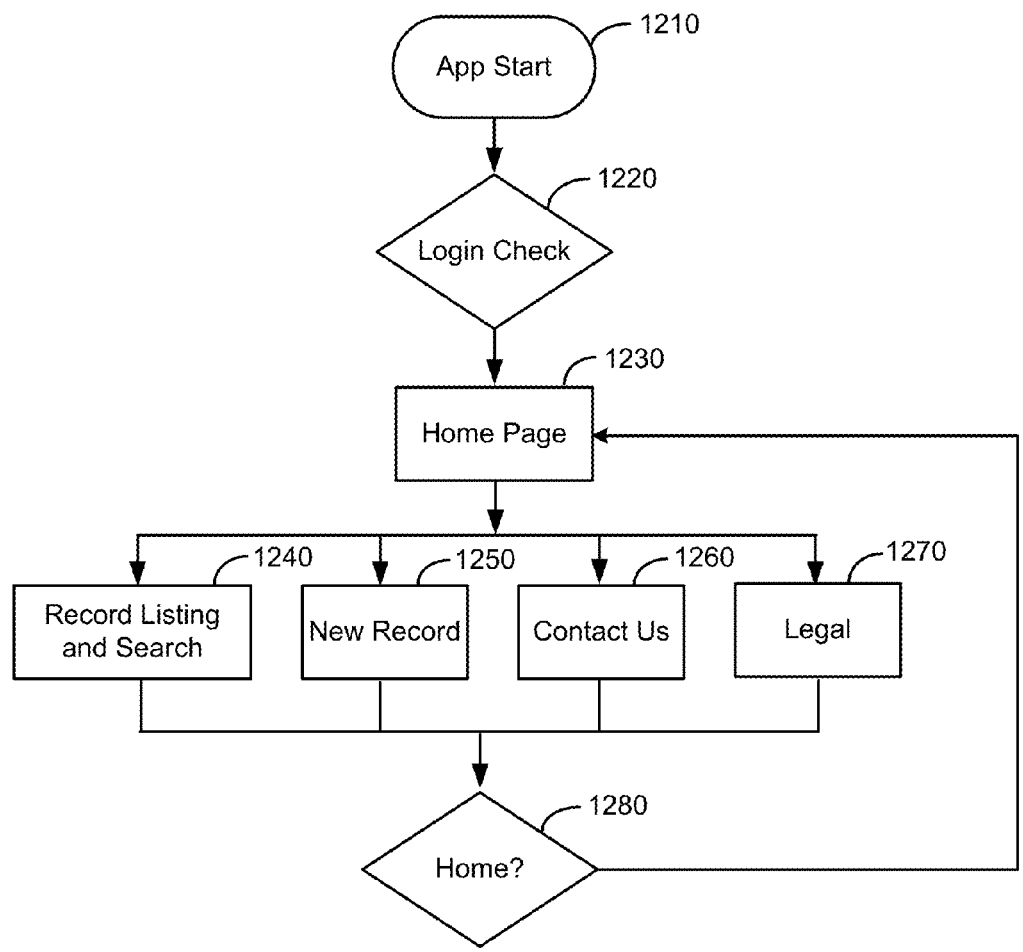
FIG. 12 is a simplified flow diagram illustrating graphical user interface logic for the top level functions for modifying a lens prescription for an eye measurement device.
Figure 13A:
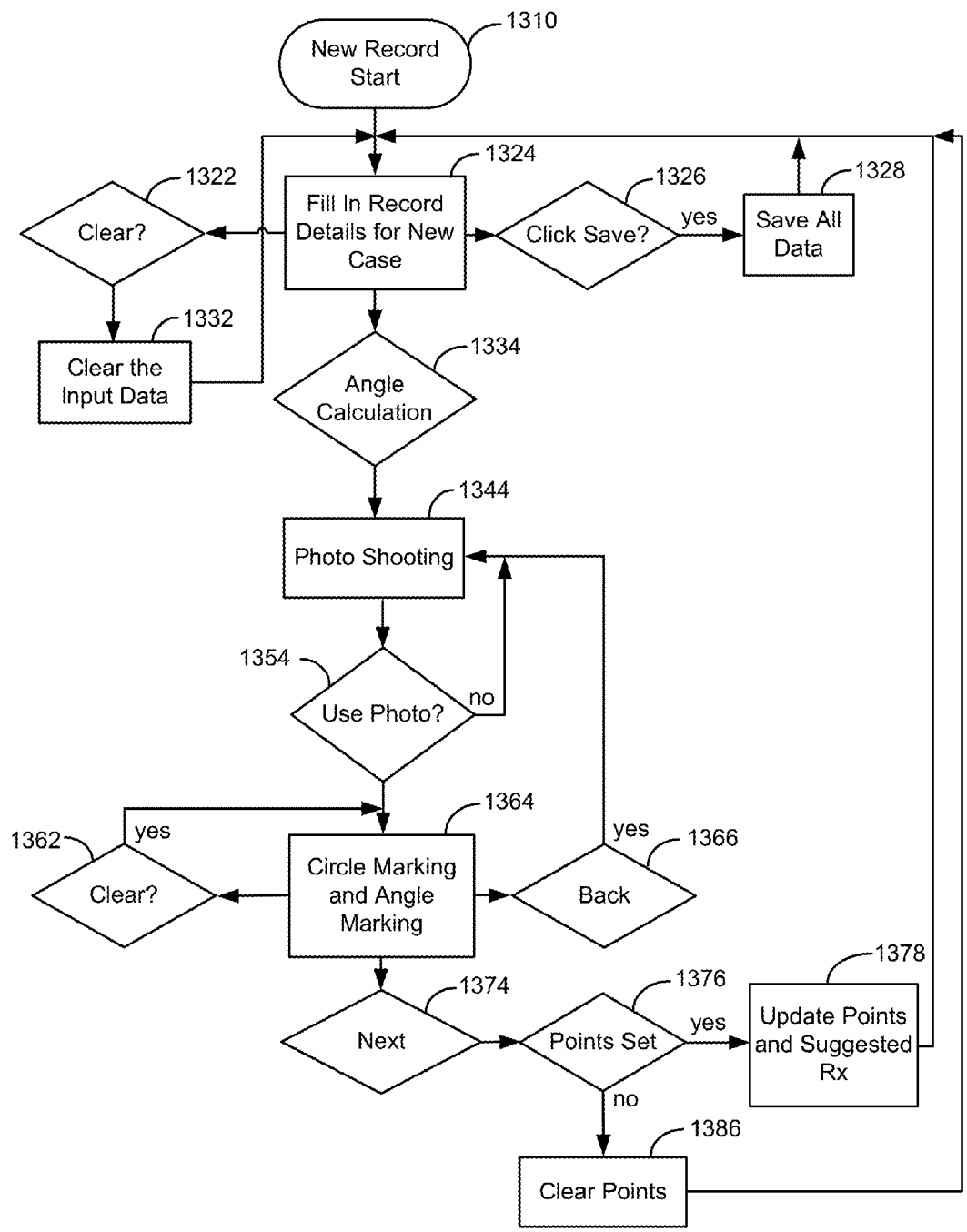
FIG. 13A is a simplified flow diagram illustrating graphical user interface logic for processing a new record for a new patient for an eye measurement device.

FIG. 12 shows graphical user interface logic for a method responsive to user inputs via graphical constructs described above. In step 1210, the application starts. Step 1220 covers login to the application. Upon successful login, in step 1230 the processor 203 delivers a home page graphical construct 381; an example home page is shown in FIG. 3B. Step 1240 is for the option for record listing and search, which is described in more detail in FIG. 14. At step 1250, the processor 203 provides a graphical element for entering a new record. The new record overview is shown in FIG. 13A. In one example, the element can be labeled New Case 362. In step 1260 the processor delivers icons for contact us 372, 382. Upon selection, content for contacting the business is listed. In step 1270, legal statements are displayed when the icon for Terms of Service 371, 383 is selected. In step 1280, the application returns to display the home page graphical construct 381.

FIG. 13A shows details of the graphical user interface logic for processing a new record, referenced in step 1250. At step 1310, the processor displays a GUI frame for starting a new record, and at step 1324, prompts are provided for filling in record details for a new case as shown in FIG. 3C. If the fields are not already clear (step 1322) then the processor 203 clears any unwanted data in step 1332. At step 1326, a save icon 915 graphical element, displayed in the GUI by processor 203, can be selected at step 1328 to save all the data. At step 1334, the processor 203 generates a series of frames that guide the angle calculation process, as described above and shown in FIG. 4A-FIG. 4D. At step 1344, photo shooting refers to selecting graphical construct 480 to capture the image of the eye. In step 1354 the processor displays a frame like that of FIG. 5A, including button constructs, which, when selected, cause the image to be used (555) for angle computations or to be discarded (550). In step 1364, the processor 203 delivers the frames for circle marking and angle marking. At step 1362 the processor provides graphical prompts that allow a user to clear (button 753 in FIG. 6) or use (button construct 754 in FIG. 6) location data, or to go back (button 751 in FIG. 6) to capture replacement location inputs, after selection of dots for identifying lens location. Processor 203 also provides graphical prompts for clear 766 or use 768 the location data and resultant element. At step 1366 the option is to go back 764 to capture a replacement eye image at step 1344 after a resultant circle graphical element has been displayed. Step 1374 continues the process when the location inputs have been accepted for use via button constructs 754, 768. In step 1376, points are accepted as set, and at step 1378 the points are updated and can be stored in the read/write memory 208, and the prescription is updated. If the points are cleared, as in step 1386, the process returns to step 1324.

Figure 13B:
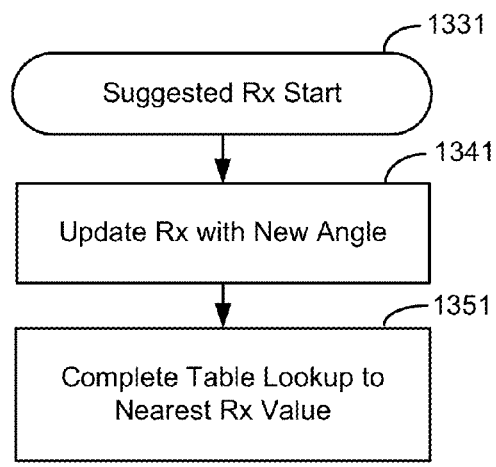
FIG. 13B is a simplified flow diagram illustrating graphical user interface logic for processing a prescription for an eye measurement device.

FIG. 13B step 1331 starts the prescription updating logic block. At step 1341, the processor 203 updates the prescription based on the determined angle of repose, and a table lookup to determine the nearest Rx value is listed in step 1351.

Figure 13C:
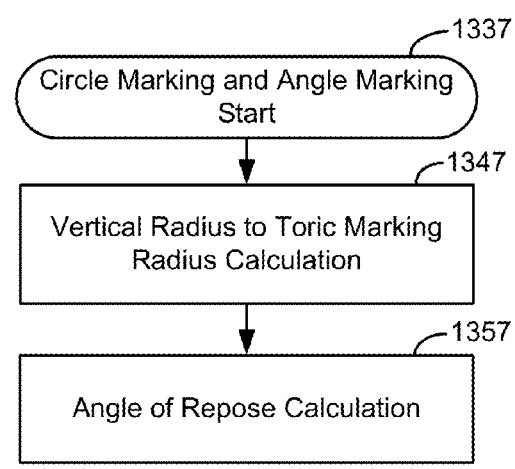
FIG. 13C is a simplified flow diagram illustrating graphical user interface logic for marking locations for an eye measurement device.

FIG. 13C shows the control logic for circle marking and angle marking. In step 1337, processor 203 executes a graphical user interface in which the GUI displays a frame or frames including the captured eye image, and graphical constructs prompt input identifying a set of locations on the captured image usable to define a location of a lens in the image, and a location usable to define an index point location on the lens, as shown in FIG. 6-FIG. 7. At step 1347 for calculating the vertical radius to toric marking radius, the processor 203 accepts input data responsive to the graphical constructs that identify locations on the captured image. At step 1357 for calculating the angle of repose, the processor 203 interprets the input data as locations on edges of a lens in the captured image, and a location of a position of an index point on the lens in the captured image, and processes the input identifying the set of locations to determine a center of the lens in the captured image, and to determine the angle of repose of the contact lens on the eye.

Figure 14:
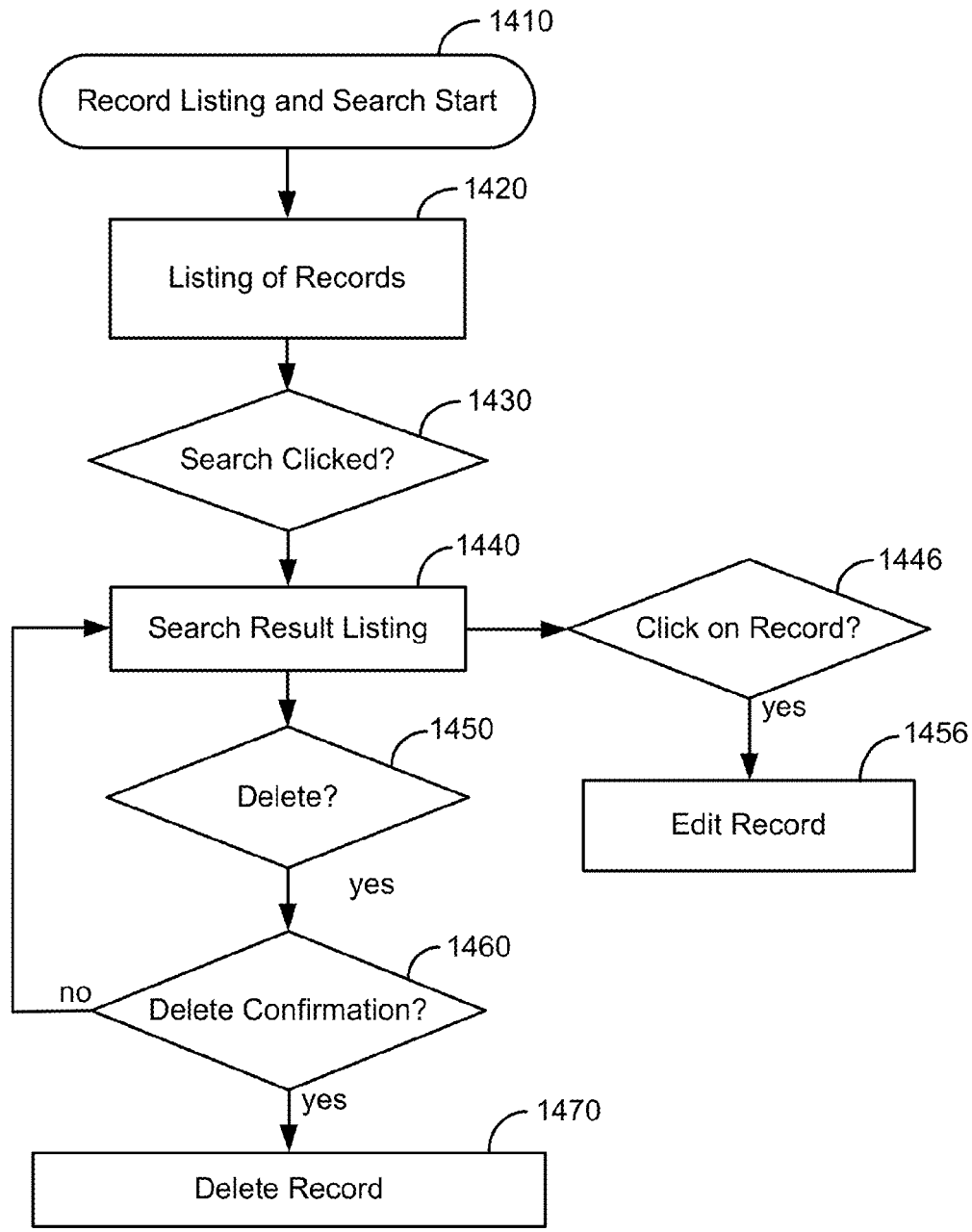
FIG. 14 is a simplified flow diagram illustrating graphical user interface logic showing the basic steps for listing and searching records, and for editing records for an eye measurement device.

FIG. 14 shows control logic for processing a record listing and search, starting with step 1410. This option can be selected using the record listing and search icon 361 shown in FIG. 3B. At step 1420, the processor 203 displays a listing of records from the patient records stored in the read/write memory 208. At step 1430 a search selection is accepted by processor 203, and at step 1440 a search result listing is displayed. At step 1446, the record can be selected for editing in step 1456. Alternatively, a search result record can be selected to delete in step 1450, and after confirmation of the intention to delete in step 1460, the processor 203 will delete the record in step 1470 from the patient records stored in the read/write memory 208.

Figure 15:
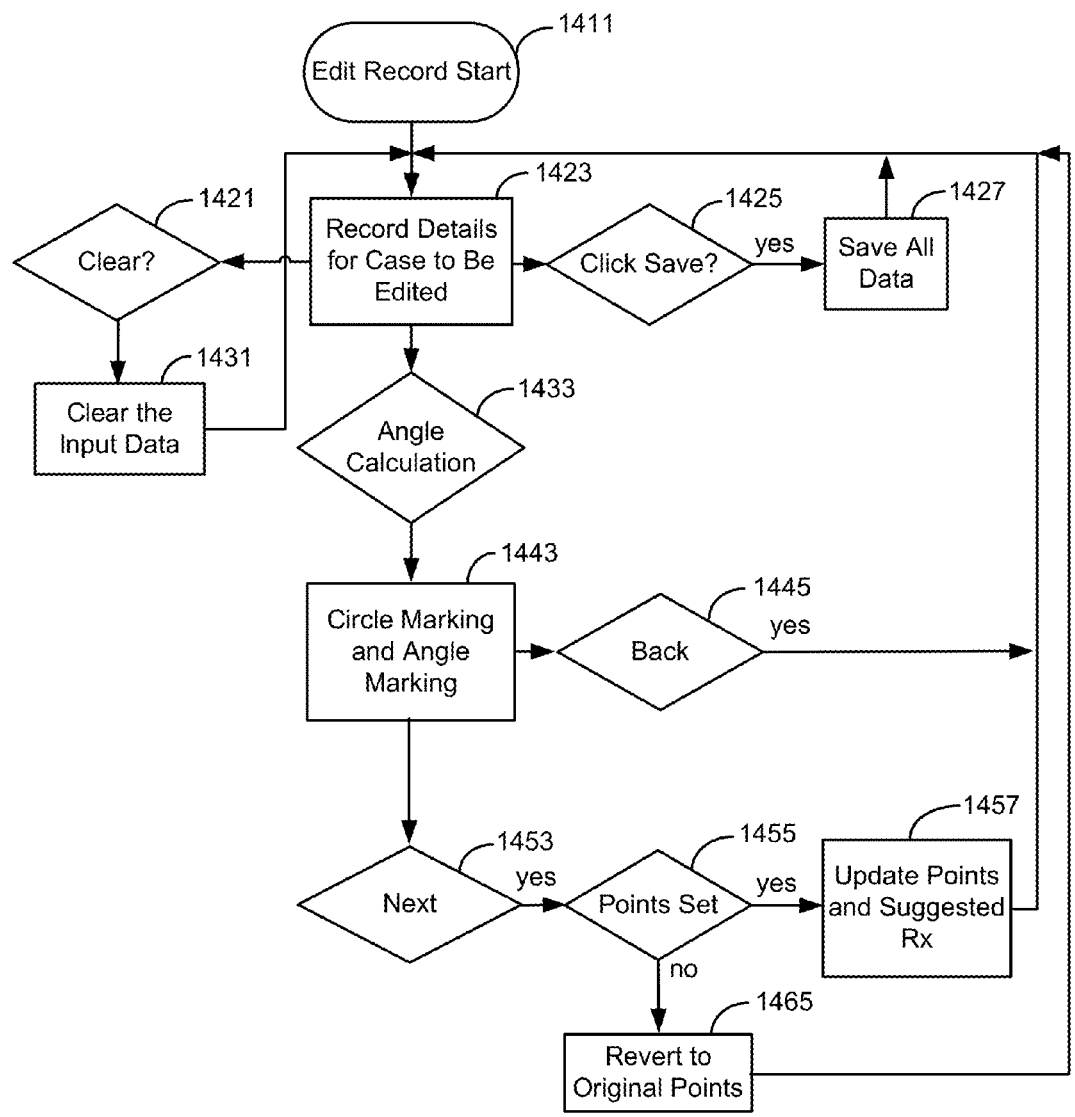
FIG. 15 is a simplified flow chart for editing a record, and for angle calculation and lens specification processes.

An existing patient record can be edited to add new location data, or to replace existing location data, for updating a prescription based on the determined angle of repose. FIG. 15 shows control logic for processing a record edit, starting with step 1411. At step 1423, prompts are provided for filling in record details in the case being edited. If the fields are not clear (step 1421) then the processor 203 clears any unwanted data in step 1431. In step 1425, a save prompt can be selected to select step 1427 to save all the data. At step 1433, the processor 203 generates a series of frames that guide the angle calculation process, as described above and shown in FIG. 4A-FIG. 4D. In step 1443, described above and in FIG. 13C, the processor 203 delivers the frames for circle marking and angle marking. Processor 203 provides graphical prompts that allow a user to go back via step 1445, returning to step 1423, described above. Processor 203 also provides graphical prompts for clear 766 or use 768 of the location data and resultant element. Step 1453 continues the process when the location inputs have been accepted for use 754 768. In step 1455, points are accepted as set, and at step 1457 the processor 203 updates the points and stores updated data for the record in the read/write memory 208, and the prescription is updated. If the points are cleared, as in step 1465, the processor 203 reverts the data to the original points and the process returns to step 1423.

Figure 16:
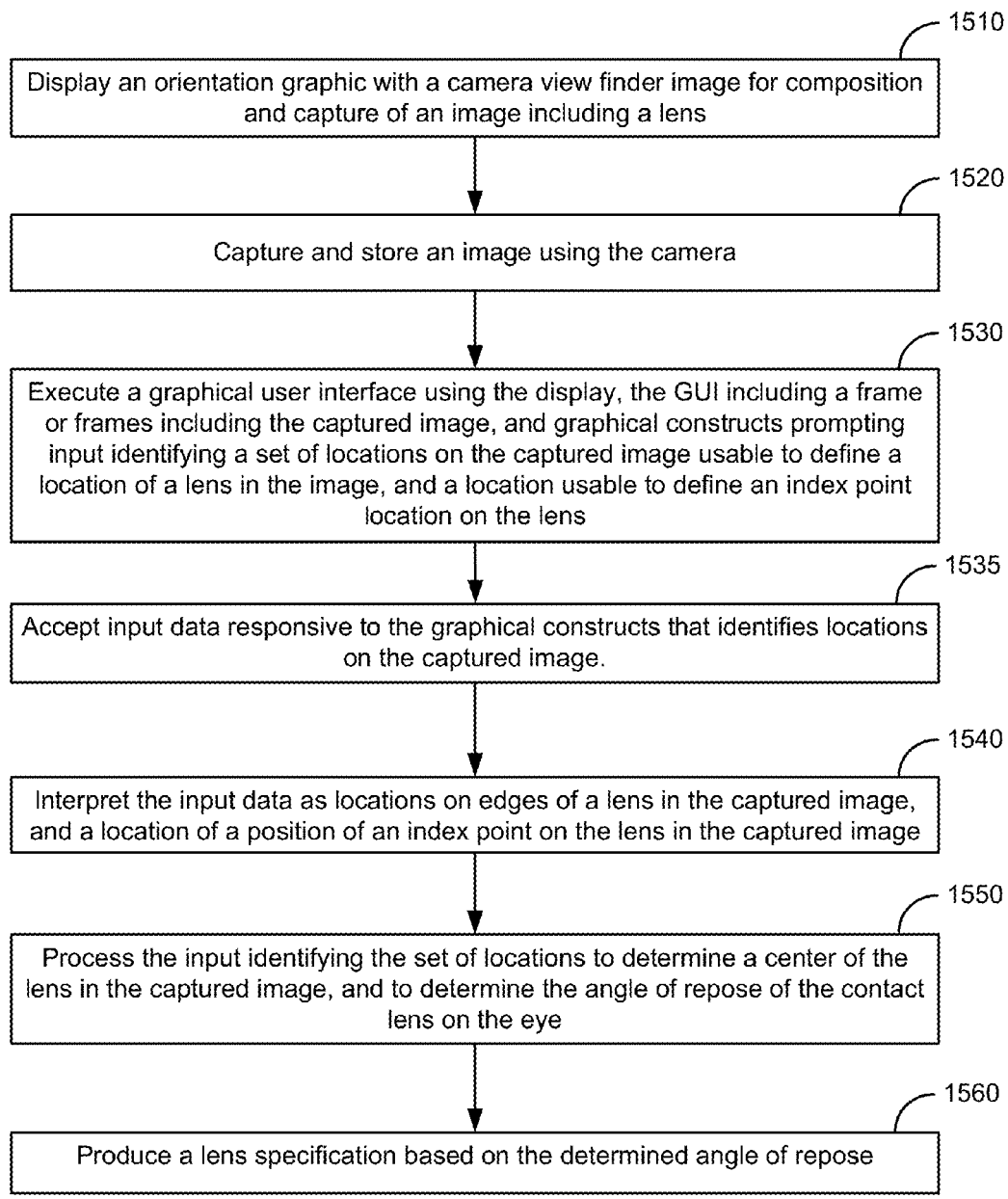
FIG. 16 is a simplified flowchart showing a method of operating a device or devices for measuring an angle of repose and updating a lens specification.

FIG. 16 shows an overview of a method for computing the angle of repose for a lens on an eye, and for modifying a specification of a contact lens using the angle. Other implementations may perform the actions in different orders and/or with different, fewer or additional actions than those illustrated in FIG. 15. Multiple actions can be combined in some implementations. In step 1510, the method includes displaying an image of a camera view finder and an orientation graphic, including indicators of orientation of the camera using the orientation sensor. These indicators can indicate rotation of the camera lens relative to a line of sight axis normal to the lens, around a horizontal axis and around a vertical axis. In step 1520, the method includes enabling capture and storage of an image while displaying the graphic. In step 1530, the method includes executing GUI logic using the display, the GUI logic including a frame or frames including the captured image and graphical constructs prompting input identifying a set of locations on the captured image, the set including a number of locations usable to define a location of a lens in the image, and a location usable to define an index point location on the lens. Step 1535 includes accepting input data, responsive to the graphical constructs, that identifies locations on the captured image.

Step 1540 includes interpreting the input data as locations on edges of a lens in the captured image, and a location of a position of an index point on the lens in the captured image, and step 1550 includes processing the input identifying the set of locations to determine the angle of repose of the lens on the eye. Finally, step 1560 of the method includes updating or producing a lens specification (e.g. a toric contact lens prescription) based on the determined angle of repose.

As with all flowcharts herein, it will be appreciated that many of the steps can be combined, performed in parallel or performed in a different sequence without affecting the functions achieved. In some cases, as the reader will appreciate, a re-arrangement of steps will achieve the same results only if certain other changes are made as well. In other cases, as the reader will appreciate, a re-arrangement of steps will achieve the same results only if certain conditions are satisfied. Furthermore, it will be appreciated that the flow charts herein show steps that are pertinent to an understanding of the invention, and it will be understood that numerous additional steps for accomplishing other functions can be performed before, after and between those shown.

While the present invention is disclosed by reference to the preferred embodiments and examples detailed above, it is to be understood that these examples are intended in an illustrative rather than in a limiting sense. It is contemplated that modifications and combinations will readily occur to those skilled in the art, which modifications and combinations will be within the spirit of the invention and the scope of the following claims.

What is claimed is:

1. A method for operating a device or devices to determine an angle of repose of a contact lens on an eye, the device or devices including a display, a camera with a camera lens, an orientation sensor, a data processor, and a user input device, comprising:
    displaying a view finder image from the camera on the display prior to capturing the image;
    displaying an orientation graphic on the display using the orientation sensor while displaying the view finder image, the orientation graphic to indicate orientation of the camera lens around a line of sight axis normal to the camera lens around a horizontal axis and around a vertical axis;
    capturing and storing an image using the camera;
    executing a graphical user interface using the display, the graphical user interface including a frame or frames including the captured image, and graphical constructs prompting input identifying a set of locations on the captured image usable to define a location of the contact lens in the image, and a location usable to define an angle of repose of the contact lens in the image; and
    accepting input data responsive to the graphical constructs that identifies the set of locations to define the location of the contact lens in the captured image and the location to define the angle of response of the contact lens in the captured image.

2. The method of claim 1, including processing the input data to determine the angle of repose of the contact lens in the captured image.

3. The method of claim 1, wherein the graphical constructs prompting input identifying a set of locations include a construct which when selected identifies a particular member of the set of locations, and causes the graphical user interface to interpret coordinates of a selected point in the displayed image as the particular member of the set of locations.

4. The method of claim 1, wherein the graphical constructs prompting input identifying a set of locations includes:
    a set of constructs corresponding to locations usable to define a perimeter of the contact lens in the captured image, where the constructs in the set when selected identify respective members of the set of locations, and cause the graphical user interface to interpret coordinates of a selected point in the captured image as the respective member of the set of locations; and
    another construct corresponding to an index point location in the set of locations usable to define the location of an index point on the contact lens in the captured image which when selected identifies the index point location, and causes the graphical user interface to interpret coordinates of a selected point in the captured image as the index point location in the set of locations.

5. The method of claim 1, including:
    interpreting the input data as locations on edges of the contact lens in the captured image, and a location of a position of an index point on the contact lens in the captured image; and
    processing the input identifying the set of locations to determine a center of the contact lens in the captured image, and to determine the angle of repose of the contact lens on an eye.

6. The method of claim 1, including:
    processing the input data to determine the angle of repose of the contact lens on an eye; and
    producing a lens specification based on the determined angle of repose.

7. The method of claim 1, wherein the user input device includes a touch screen overlying the display.

8. The method of claim 1, wherein the orientation graphic overlies the view finder image on the display, and includes a feature useable as reference for sizing the contact lens within the area of the captured image.

9. A device for determining an angle of repose of a contact lens on an eye, comprising:
    a display; a camera with a camera lens, a data processor; an orientation sensor and a user input device, and including instructions executable by the data processor to:
    display a view finder image from the camera on the display prior to capturing an image;
    display an orientation graphic on the display using the orientation sensor while displaying the view finder image, the orientation graphic including graphical constructs that indicate orientation of the camera lens around a line of sight axis normal to the camera lens, around a horizontal axis and around a vertical axis;
    store an image captured using the camera;
    execute a graphical user interface using the display, the graphical user interface including a frame or frames including the captured image, and graphical constructs prompting input identifying a set of locations on the captured image usable to define a location of the contact lens in the image, and a location usable to define an angle of repose of the contact lens in the image; and
    accept input data responsive to the graphical constructs that identifies the set of locations to define the location of the lens in the captured image and the location to define the angle of response of the contact lens in the captured image.

10. The device of claim 9, including instructions executable to process the input data to determine the angle of repose.

11. The device of claim 9, wherein the graphical constructs prompting input identifying a set of locations include a construct which when selected identifies a particular member of the set of locations, and causes the graphical user interface to interpret coordinates of a selected point in the displayed image as the particular member of the set of locations.

12. The device of claim 9, wherein the graphical constructs prompting input identifying a set of locations include:
   a set of constructs corresponding to locations usable to define a perimeter of the contact lens in the captured image, where the constructs in the set when selected identify respective members of the set of locations, and cause the graphical user interface to interpret coordinates of a selected point in the captured image as the respective member of the set of locations; and
   another construct corresponding to an index point location in the set of locations usable to define the location of an index point on the contact lens in the captured image which when selected identifies the index point location, and causes the graphical user interface to interpret coordinates of a selected point in the captured image as the index point location in the set of locations.

13. The device of claim 9, including instructions executable to:
   interpret the input data as locations on edges of the contact lens in the captured image, and a location of a position of an index point on the lens in the captured image; and
   process the input identifying the set of locations to determine a center of the contact lens in the captured image, and to determine the angle of repose of the lens.

14. The device of claim 9, including instructions executable to:
   process the input data to determine the angle of repose of the contact lens on an eye; and
   produce a lens specification based on the determined angle of repose.

15. The device of claim 9, wherein the user input device includes a touch screen overlying the display.

16. The device of claim 9, wherein the orientation graphic overlies the view finder image on the display, and includes a feature useable as reference for sizing the contact lens within the area of the captured image.

17. A computer program product for determining an angle of repose of a contact lens on an eye using a device having a display; a camera with a camera lens, a data processor, an orientation sensor and a user input device, the product comprising a non-transitory computer readable medium storing instructions executable by the data processor, the instructions comprising:
   logic to display a view finder image from a camera on the display prior to capturing the image;
   logic to display an orientation graphic on the display while displaying the view finder image, using the orientation sensor, the orientation graphic including graphical constructs that indicate orientation of the camera lens around a line of sight axis normal to the cameral lens, around a horizontal axis and around a vertical axis;
   logic to store an image captured using the camera;
   logic to execute a graphical user interface using the display, the graphical user interface including a frame or frames including the captured image, and graphical constructs prompting input identifying a set of locations on the captured image usable to define a location of the contact lens in the image, and a location usable to define an angle of repose of the contact lens in the image; and
   logic to accept input data responsive to the graphical constructs that identifies the set of locations to define the location of the contact lens in the captured image and the location to define the angle of repose of the contact lens in the captured image.

18. The product of claim 17, wherein the instructions include logic to process the input data to determine the angle of repose of the contact lens on the capture image.

19. The product of claim 17, wherein the graphical constructs prompting input identifying a set of locations include a construct which when selected identifies a particular member of the set of locations, and causes the graphical user interface to interpret coordinates of a selected point in the displayed image as the particular member of the set of locations.

20. The product of claim 17, wherein the graphical constructs prompting input identifying a set of locations include:
   a set of constructs corresponding to locations usable to define a perimeter of the contact lens in the captured image, where the constructs in the set when selected identify respective members of the set of locations, and cause the graphical user interface to interpret coordinates of a selected point in the captured image as the respective member of the set of locations; and
   another construct corresponding to an index point location in the set of locations usable to define location of an index point on the contact lens in the captured image which when selected identifies the index point location, and causes the graphical user interface to interpret coordinates of a selected point in the captured image as the index point location in the set of locations.

21. The product of claim 17, wherein the instructions include logic to:
   interpret the input data as locations on edges of the contact lens in the captured image, and a location of a position of an index point on the contact lens in the captured image; and
   process the input identifying the set of locations to determine a center of the contact lens in the captured image, and to determine the angle of repose of the contact lens.

22. The product of claim 17, wherein the instructions include logic to:
   process the input data to determine the angle of repose of the contact lens; and
   produce a lens specification based on a determined angle of repose.

23. The product of claim 17, wherein the user input device includes a touch screen overlying the display.

24. The product of claim 17, wherein the orientation graphic overlies the view finder image on the display, and includes a feature useable as reference for sizing the contact lens within the area of the captured image.

* * * * *

UNITED STATES PATENT AND TRADEMARK OFFICE
CERTIFICATE OF CORRECTION

PATENT NO. : 9,867,533 B2
APPLICATION NO. : 15/070254
DATED : January 16, 2018
INVENTOR(S) : Chi Shing Fan Page 1 of 1

It is certified that error appears in the above-identified patent and that said Letters Patent is hereby corrected as shown below:

In the Specification

In Column 2, Line 5, delete the word "site" and insert the word -- sight --.

In Column 4, Line 9, delete the word "non-transistor" and insert the word -- non-transitory --.

In Column 9, Line 22, delete the phrase "construct 742" and insert the phrase -- construct 752 --.

In the Claims

In Claim 1, Column 13, Line 46, delete the word "response" and insert the word -- repose --.

In Claim 9, Column 13, Line 56, delete the word "response" and insert the word -- repose --.

In Claim 17, Column 15, Line 52, delete the word "cameral" and insert the word -- camera --.

In Claim 18, Column 16, Line 11, delete the word "capture" and insert the word -- captured --.

Signed and Sealed this
Twelfth Day of June, 2018

Andrei Iancu
*Director of the United States Patent and Trademark Office*